(12) United States Patent
Raslambekov

(10) Patent No.: US 11,766,312 B1
(45) Date of Patent: Sep. 26, 2023

(54) SYSTEMS AND METHODS FOR DETERMINING AN ORTHODONTIC TREATMENT

(71) Applicant: Oxilio Ltd, Larnaca (CY)

(72) Inventor: Islam Khasanovich Raslambekov, Long Island City, NY (US)

(73) Assignee: Oxilio Ltd, Larnaca (CY)

( * ) Notice: Subject to any disclaimer, the term of this patent is extended or adjusted under 35 U.S.C. 154(b) by 0 days.

(21) Appl. No.: 17/980,950

(22) Filed: Nov. 4, 2022

(51) Int. Cl.
| | |
|---|---|
| *A61C 7/00* | (2006.01) |
| *A61C 9/00* | (2006.01) |
| *G16H 50/50* | (2018.01) |
| *G06T 17/20* | (2006.01) |
| *G16H 20/40* | (2018.01) |
| *A61C 7/08* | (2006.01) |

(52) U.S. Cl.
CPC ............ *A61C 7/002* (2013.01); *A61C 7/08* (2013.01); *A61C 9/0046* (2013.01); *G06T 17/20* (2013.01); *G16H 20/40* (2018.01); *G16H 50/50* (2018.01)

(58) Field of Classification Search
CPC .. A61C 5/20; A61C 7/08; A61C 7/002; A61C 9/0046; G16H 20/40; G16H 30/20; G16H 50/50; A61B 5/4833
See application file for complete search history.

(56) References Cited

U.S. PATENT DOCUMENTS

| | | | |
|---|---|---|---|
| 6,602,070 B2 | 8/2003 | Miller et al. | |
| 10,342,638 B2 | 7/2019 | Kitching et al. | |
| 10,524,879 B2 | 1/2020 | Kitching et al. | |
| 10,548,690 B2 | 2/2020 | Wen | |
| 10,856,954 B1 | 12/2020 | Raslambekov | |
| 10,950,061 B1 | 3/2021 | Raslambekov | |
| 10,993,782 B1 * | 5/2021 | Raslambekov | ...... A61B 5/4833 |
| 11,026,767 B1 | 6/2021 | Raslambekov | |
| 11,058,515 B1 * | 7/2021 | Raslambekov | .......... A61C 7/08 |
| 11,191,618 B1 | 12/2021 | Raslambekov | |
| 11,259,897 B1 * | 3/2022 | Raslambekov | ........ G16H 30/20 |
| 11,328,809 B1 * | 5/2022 | Raslambekov | ........ G16H 20/40 |

(Continued)

FOREIGN PATENT DOCUMENTS

WO 2017172537 A1 10/2017

OTHER PUBLICATIONS

U.S. Appl. No. 16/704,718, filed Dec. 5, 2019.

*Primary Examiner* — Yogesh P Patel
(74) *Attorney, Agent, or Firm* — BCF LLP

(57) ABSTRACT

A method and a system for determining an orthodontic treatment for a subject are provided. The method comprises: obtaining an indication of a current and target position of the given tooth; determining a tooth movement trajectory of the given tooth during the orthodontic treatment, the tooth trajectory defining a path of the given tooth from the current to the target position, the determining the tooth trajectory comprising determining a movement of the given tooth along the tooth trajectory by: determining, a plurality of movement components for the given tooth to be performed to displace from the current to the target position; obtaining, for a given one of the plurality of movement components, a respective magnitude value, the respective magnitude value being indicative of a path length at which the given tooth is to displace towards the target position thereof performing the given one of the plurality of movement components.

20 Claims, 10 Drawing Sheets

(56) References Cited

U.S. PATENT DOCUMENTS

| | | | |
|---|---|---|---|
| 11,364,103 B1 | 6/2022 | Raslambekov | |
| 11,517,400 B1* | 12/2022 | Raslambekov | G16H 20/40 |
| 2009/0191503 A1* | 7/2009 | Matov | A61C 7/20 |
| | | | 433/2 |
| 2017/0100208 A1 | 4/2017 | Wen | |
| 2017/0100213 A1* | 4/2017 | Kuo | G16H 20/40 |
| 2017/0273760 A1 | 9/2017 | Morton et al. | |
| 2020/0000552 A1* | 1/2020 | Mednikov | A61C 5/20 |
| 2020/0345455 A1* | 11/2020 | Roein Peikar | A61C 7/146 |
| 2022/0079714 A1* | 3/2022 | Paraketsov | G06T 17/20 |
| 2022/0304774 A1* | 9/2022 | Wratten, Jr. | A61C 7/002 |

\* cited by examiner

SYSTEMS AND METHODS FOR DETERMINING AN ORTHODONTIC TREATMENT

FIELD

The present technology relates to systems and methods for determining an orthodontic treatment for a subject.

BACKGROUND

In orthodontics, planning an orthodontic treatment for a subject may include determining a tooth trajectory for each tooth of a subject's arch form. This may further include modelling tooth movements of a given tooth in the course of the planned orthodontic treatment: from an initial (current) position to a target position of the given tooth, the target position being typically associated with alignment of the given tooth within the subject's arch form.

Further, once the tooth movements have been modelled, an orthodontic device, such as an aligner (or a set thereof), may be produced and applied to the subject's arch form to exert an external force, over a predetermined treatment interval, onto the given tooth causing it to move, along the so determined tooth trajectory, towards the target position.

However, there are certain contrasting requirements related to the orthodontic treatment: (1) efficiency requirement—minimizing an overall duration of the orthodontic treatment, and (2) safety requirement—ensuring that the planned orthodontic treatment does not cause damage to the subject's teeth or other buccal anatomical structures through collisions or excess applied forces.

Certain prior art approaches have been proposed for generating the tooth trajectory for the given tooth considering the above-identified technical problem.

United States Patent Application Publication No.: 2017/0273,760-A1 published on Sep. 28, 2017, assigned to Align Technology Inc, and entitled "SYSTEMS, METHODS, AND DEVICES FOR PREDICTABLE ORTHODONTIC TREATMENT" discloses a system for generating a treatment plan for repositioning a plurality of teeth, the system comprising instructions to receive a digital data set representing the plurality of teeth, and determine a movement trajectory for repositioning, each tooth from an initial position and orientation towards a target position and orientation. The movement trajectory of at least one tooth comprises movement along a plurality of different directions. A movement velocity is determined for repositioning each tooth along the corresponding movement trajectory. The movement velocity is determined independently for each tooth, and the movement velocity for the at least one tooth is determined independently for each direction.

U.S. Pat. No. 10,524,879-B2 issued on Jan. 7, 2020, assigned to Align Technology Inc, and entitled "AUTOMATED TREATMENT STAGING FOR TEETH" discloses an apparatus, system, and methods for utilizing one or more computing devices to stage the movement of teeth during an alignment treatment. The computing device receives an electronic representation of the patient's teeth in their initial position and an electronic representation of the teeth a final position for each tooth. A route each tooth will travel to reach its final position is determined, and the teeth are scheduled to move according to a movement pattern. Moreover, the schedule of movement takes into account a maximum rate of tooth movement for each tooth, the path of movement for each tooth, the distance each tooth needs to move, any needed tooth staggering, any needed round-tripping or tooth movement slowing. The invention also includes techniques for determining an optimum number of stages for the treatment based on the schedule of movement.

U.S. Pat. No. 10,548,690-B2 issued on Feb. 4, 2020, assigned to Ulab Systems Inc, and entitled "ORTHODONTIC PLANNING SYSTEMS" discloses systems and methods for treating teeth to correct for malocclusions. The methods include receiving a scanned dental model of a subject's dentition, determining a treatment plan having a plurality of incremental movements for repositioning one or more teeth of the subject's dentition, and fabricating one or more aligners correlating to a first subset of the plurality of incremental movements.

U.S. Pat. No. 6,602,070-B2 issued on Aug. 5, 2003, assigned to Align Technology Inc, and entitled "SYSTEMS AND METHODS FOR DENTAL TREATMENT PLANNING" discloses computer-implemented systems and methods implement a dental treatment plan by specifying tooth movement patterns using a two-dimensional array; and generating treatment paths to move the teeth in accordance with the specified pattern.

SUMMARY

It is an object of the present technology to ameliorate at least some of the inconveniences present in the prior art.

The developers of the present technology have developed systems and method for a more accurate modelling of the tooth movements. More specifically, the present methods and systems are directed to determining a tooth movement of a given tooth along its trajectory as a plurality of tooth movement components, including, without limitation, a translation; a tipping, a torquing, a rotation, an extrusion, an intrusion, and the like.

Further, according to at least some non-limiting embodiments of the present technology, each one of these tooth movement components can be performed separately, without combining any two of them. In other words, unlike in the prior art approaches, according to certain non-limiting embodiments of the present technology, at a given moment in time, the given tooth can be caused to perform only one of the plurality of tooth movement components. This may allow (i) assigning a respective specific order for each such tooth movement component to be performed by the given tooth along its tooth trajectory, and (ii) assigning a respective speed value for the given tooth for moving along each one of the plurality of tooth movement components.

Thus, such level of granularity for defining the tooth movement can allow for a greater control over the given tooth along its tooth trajectory, which may further help in resolving possible collisions of the given tooth with neighboring or opposing teeth. Also, causing the given tooth to perform only a single one of the plurality of tooth movement components and adjusting the speed value therealong can allow adjusting the parameters of the resulting orthodontic appliance pertaining to the wear comfort thereof for the subject during the orthodontic treatment.

More specifically, in accordance with a first broad aspect of the present technology, there is provided a computer-implementable method of determining an orthodontic treatment for a subject. The method is executable by a processor of a computing device. The method comprises: obtaining, by the processor, a 3D digital model representing a surface of an arch form of the subject, the arch form including a plurality of teeth; determining, by the processor, based on the 3D digital model, a current position of a given tooth of the plurality of teeth within the arch form; obtaining, by the processor, an indication of a target position for the given tooth; determining, by the processor, based on the current and the target position of the given tooth, a tooth movement trajectory of the given tooth during the orthodontic treatment, the tooth trajectory defining a path of the given tooth from the current to the target position thereof, the determining the tooth trajectory comprising determining a movement of the given tooth along the tooth trajectory by: determining, by the processor, a plurality of movement components for the given tooth to be performed to displace from the current to the target position; obtaining, for a given one of the plurality of movement components, a respective magnitude value, the respective magnitude value being indicative of a path length at which the given tooth is to displace towards the target position thereof performing the given one of the plurality of movement components; storing, in a memory of the computing device, data of the tooth trajectory of the given tooth for further use in determining the orthodontic treatment for the subject.

In some implementations of the method, the given one of the plurality of movement components is indicative of a respective degree of freedom of the given tooth within the arch form.

In some implementations of the method, the given one of the plurality of movement components comprises one of a translation and a rotation.

In some implementations of the method, the given one of the plurality of movement components comprises one of: a translation; a tipping, a torquing, a rotation, an extrusion, and an intrusion.

In some implementations of the method, the obtaining, for the given one of the plurality of movement components, the respective magnitude value comprises obtaining the respective magnitude value for at least two ones of the plurality of movement components.

In some implementations of the method, the obtaining, for the given one of the plurality of movement components, the respective magnitude value comprises obtaining the respective magnitude value for each one of the plurality of movement components.

In some implementations of the method, the plurality of movement components includes at least two of: a translation; a tipping, a torquing, a rotation, an extrusion, and an intrusion.

In some implementations of the method, the plurality of movement components comprises the translation and the rotation.

In some implementations of the method, the orthodontic treatment comprises causing the given tooth to perform each one of the plurality of movement components separately, without combining any one thereof.

In some implementations of the method, the orthodontic treatment comprises causing the given tooth to perform each one of the plurality of movement components sequentially.

In some implementations of the method, the obtaining, for the given one of the plurality of movement components, the respective magnitude value comprises determining, by the processor, the respective magnitude value based on minimizing a time for the given tooth to displace from the current to the target position.

In some implementations of the method, prior to the storing, the method further comprises obtaining, for the given one of the plurality of movement components, a respective ordinal position thereof within the plurality of movement components of the tooth trajectory.

In some implementations of the method, prior to the storing, the method further comprises obtaining, for the given one of the plurality of movement components, a respective speed value at which the given tooth is to be caused to perform the given one of the plurality of movement components.

In some implementations of the method, the respective speed value is determined based on a predetermined threshold displacement of the given tooth in a given time interval of a plurality of time intervals of the orthodontic treatment, the plurality of treatment intervals defining, within the tooth trajectory for the given tooth, a plurality of segments of the tooth trajectory, a given segment of the plurality of segments having a respective portion of the path length at which the given tooth is to displace performing the given one of the plurality of movement components in the given time interval.

In some implementations of the method, the predetermined threshold displacement has been determined as being a maximum displacement of the given tooth in the given time interval without causing a permanent damage to the given tooth.

In some implementations of the method, the respective portion of the path length is equal to the predetermined threshold displacement.

In some implementations of the method, the given time interval has a predetermined duration.

In some implementations of the method, each one of the plurality of time intervals has an equal duration.

In some implementations of the method, the orthodontic treatment comprises applying, to at least some of the plurality of teeth, during the given time interval, a respective orthodontic appliance configured to cause the given tooth to displace at the respective portion of the path length by performing the given one of the plurality of movement components.

In some implementations of the method, the respective orthodontic appliance comprises an orthodontic aligner.

Further, in accordance with a second broad aspect of the present technology, there is provided a computing device for determining an orthodontic treatment for a subject. The computing device comprises a processor and a non-transitory computer-readable memory storing instructions. The processor, upon executing the instructions, is configured to: obtain a 3D digital model representing a surface of an arch form of the subject, the arch form including a plurality of teeth; determine, based on the 3D digital model, a current position of a given tooth of the plurality of teeth within the arch form; obtain an indication of a target position for the given tooth; determine, based on the current and the target position of the given tooth, a tooth movement trajectory of the given tooth during the orthodontic treatment, the tooth trajectory defining a path of the given tooth from the current to the target position thereof, determining the tooth trajectory comprising determining a movement of the given tooth along the tooth trajectory by: determining, a plurality of movement components for the given tooth to be performed to displace from the current to the target position; obtaining, for a given one of the plurality of movement components, a respective magnitude value, the respective magnitude value being indicative of a path length at which the given tooth is to displace towards the target position thereof performing the given one of the plurality of movement components; store, in in the non-transitory computer-readable memory, data of the tooth trajectory of the given tooth for further use in determining the orthodontic treatment for the subject.

In the context of the present specification, unless expressly provided otherwise, a computer system may refer, but is not limited to, an "electronic device", an "operation system", a "system", a "computer-based system", a "controller unit", a "control device" and/or any combination thereof appropriate to the relevant task at hand.

In the context of the present specification, unless expressly provided otherwise, the expression "computer-readable medium" and "memory" are intended to include media of any nature and kind whatsoever, non-limiting examples of which include RAM, ROM, disks (CD-ROMs, DVDs, floppy disks, hard disk drives, etc.), USB keys, flash memory cards, solid state-drives, and tape drives.

In the context of the present specification, a "database" is any structured collection of data, irrespective of its particular structure, the database management software, or the computer hardware on which the data is stored, implemented or otherwise rendered available for use. A database may reside on the same hardware as the process that stores or makes use of the information stored in the database or it may reside on separate hardware, such as a dedicated server or plurality of servers.

Further, it should be expressly understood that, in the context of the present specification, the term "orthodontic treatment" is broadly referred to as any type of medical intervention aimed at correcting malocclusions associated with the patient, including surgical and non-surgical manipulations, such as, but not limited to, using aligners. Further, the orthodontic treatment, as referred to herein, may be determined by a professional practitioner in the field of dentistry (such as an orthodontist, a maxillofacial surgeon, for example), or automatically by a specific software, based on respective image data and input parameters associated with the patient.

In the context of the present specification, unless expressly provided otherwise, the words "first", "second", "third", etc. have been used as adjectives only for the purpose of allowing for distinction between the nouns that they modify from one another, and not for the purpose of describing any particular relationship between those nouns.

Embodiments of the present technology each have at least one of the above-mentioned object and/or aspects, but do not necessarily have all of them. It should be understood that some aspects of the present technology that have resulted from attempting to attain the above-mentioned object may not satisfy this object and/or may satisfy other objects not specifically recited herein.

Additional and/or alternative features, aspects and advantages of embodiments of the present technology will become apparent from the following description, the accompanying drawings and the appended claims.

BRIEF DESCRIPTION OF THE DRAWINGS

For a better understanding of the present technology, as well as other aspects and further features thereof, reference is made to the following description which is to be used in conjunction with the accompanying drawings, where.

DETAILED DESCRIPTION

Certain aspects and embodiments of the present technology are directed to methods of and systems for determining an orthodontic treatment.

More specifically, certain aspects and embodiments of the present technology comprise a computer-implemented method for determining a tooth trajectory of a given tooth of the subject, from an initial to a target position, by determining a plurality of movement components that the given tooth needs to perform to arrive to the target position.

Certain non-limiting embodiments of the present technology minimize, reduce, or avoid some of the problems noted in association with the prior art. For example, by implementing certain embodiments of the present technology, a more effective orthodontic treatment can be determined. More specifically, the increased effectiveness of the orthodontic treatment can be achieved by determining the tooth movement of the given tooth along the tooth trajectory as including a plurality of tooth movement components that the given tooth is to perform separately, that is, one at a time, such as sequentially. This allows for more control over the tooth movement of the given tooth, which may allow more accurately determining and further preventing collisions of the given tooth with neighboring and/or opposing teeth in the course of the orthodontic treatment. This is unlike prior art approaches where the teeth are caused to perform several movement components, such as a translation and rotation, simultaneously, which has less granularity in terms of monitoring an effect of the simultaneous movements. More effective determination and prevention of the collisions can allow avoiding damaging of the subject's teeth, such as by causing chips and/or cracks to the given tooth and/or the neighboring teeth, and hence increasing the effectiveness of the treatment.

Also, an orthodontic appliance produced, according to at least some non-limiting embodiments of the present technology, to cause so planned movements of the subject's teeth would be configured to deform surrounding tissue of the given tooth only in one direction, corresponding to a given one of the plurality of the tooth movement components, which may provide for a greater wear comfort of the orthodontic appliance. Accordingly, the greater wear comfort can be associated with a better compliance of the subject to the orthodontic treatment, which may thus increase the overall effectiveness thereof even more.

Biomechanics of Tooth Movements

Figure 1:
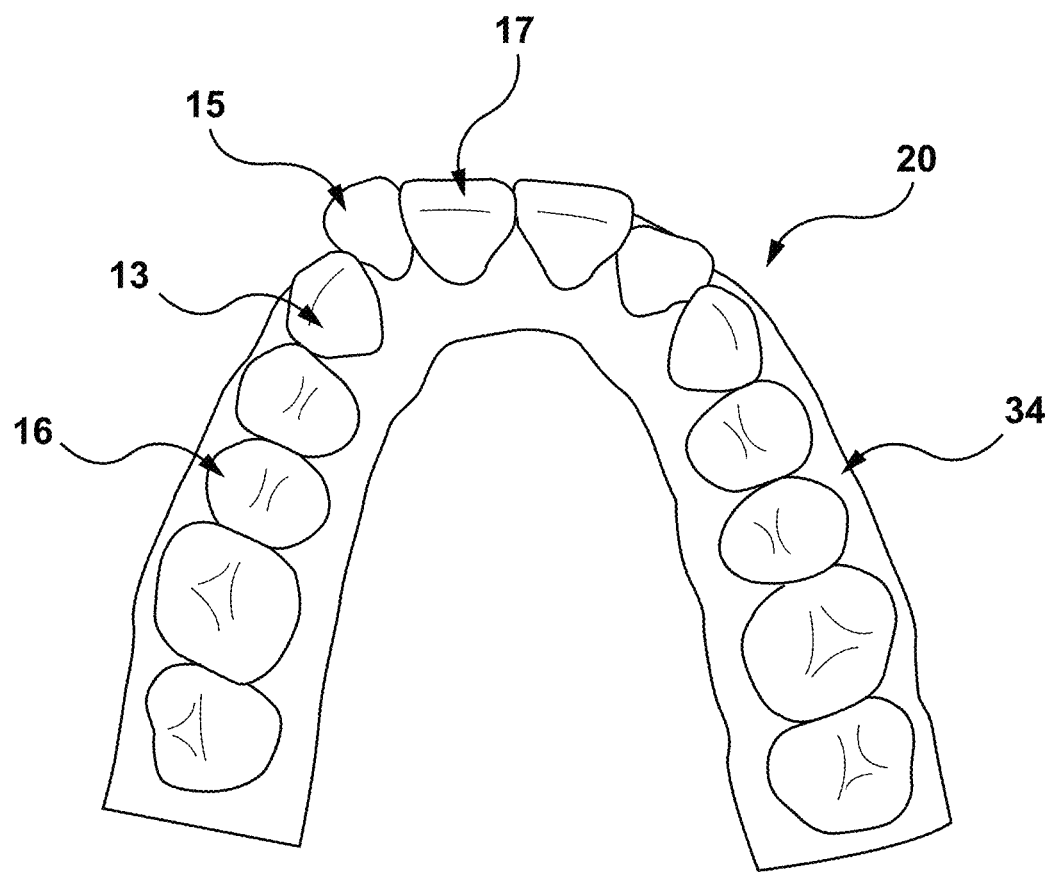
FIG. 1 is a perspective view of an upper arch form of a subject depicting respective examples of malocclusions of subject's teeth, in accordance with certain non-limiting embodiments of the present technology.

With initial reference to FIG. 1, there is depicted a bottom view of an upper arch form 20 of the subject, to which certain aspects and non-limiting embodiments of the present technology may be applied.

As it can be appreciated, the upper arch form 20 includes upper teeth 16 and an upper gingiva 34. Further, in the depicted embodiments of FIG. 1, a given tooth 15 is misaligned within the upper teeth 16 as it protrudes outwardly relative to its neighboring teeth, a first adjacent tooth 13 and a second adjacent tooth 17, and rotated clockwise around its tooth axis (not separately depicted in FIG. 1). Thus, for correcting the present misalignment of the given tooth 15, an orthodontic treatment may be provided to the subject.

In accordance with certain non-limiting embodiments of the present technology, the orthodontic treatment may comprise applying an orthodontic device. Generally speaking, the orthodontic device may be configured to exert a force onto the given tooth 15 causing it to move towards a target position thereof, that is, an aligned position, which is, in the depicted embodiments of FIG. 1, inwardly between the first adjacent tooth 13 and the second adjacent tooth 17 to align with the first adjacent tooth 13 and the second adjacent tooth 17. In various non-limiting embodiments of the present technology, the orthodontic device may comprise orthodontic appliances of different types, shapes, sizes, and configurations, such as those including, without limitation, aligners, brackets, multi-strand wires, strips, retainers, and plates.

Figure 2A:
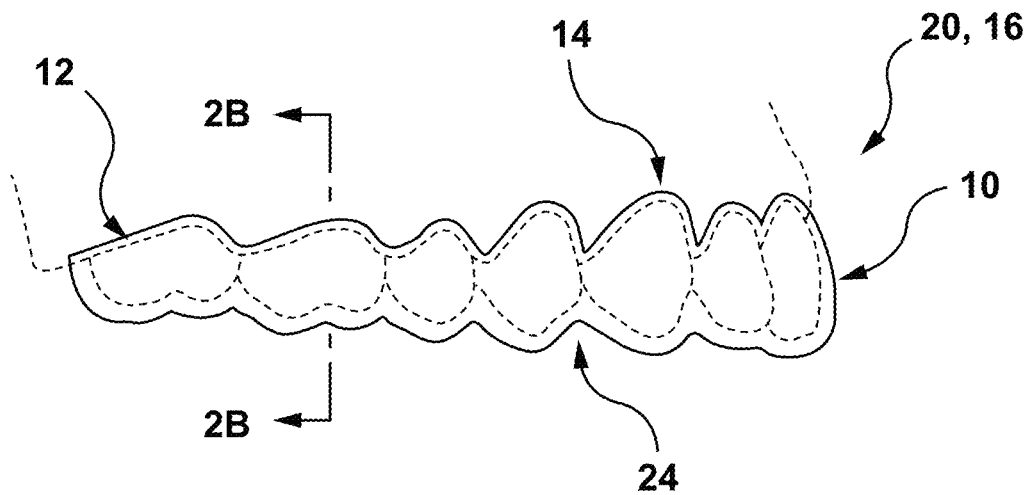
FIGS. 2A and 2B depict a side view and a cross-sectional view through line 3-3, respectively, of an orthodontic appliance applied to the subject's teeth that may be configured to treat the malocclusions of the subject's teeth present in FIG. 1, in accordance with certain non-limiting embodiments of the present technology.
Figure 2B:
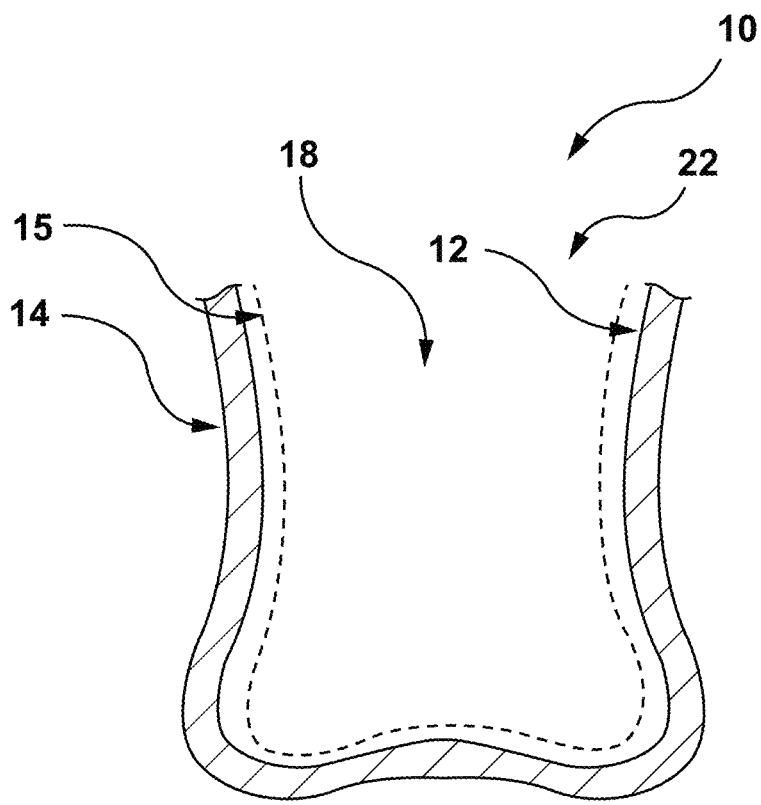

In specific non-limiting embodiments of the present the present technology, the orthodontic device may include an orthodontic aligner. With reference to FIGS. 2A and 2B, there is depicted an aligner 10 applied to at least some of the upper teeth 16, in accordance with certain non-limiting embodiments of the present technology. The aligner 10 comprises an inner surface 12 and an outer surface 14. The inner surface 12 defines a channel 18, which is configured, in some non-limiting embodiments of the present technology, for receiving crown portions of the at least some of the upper teeth 16 including the given tooth 15, as an example. However, in other non-limiting embodiments of the present technology, the channel 18 of the aligner 10 may be configured to receive crown portions of all of the upper teeth 16. At least one edge of the channel 18 is shaped for following a gum line along the upper gingiva 34.

It is appreciated that, in accordance with certain non-limiting embodiments of the present technology, the aligner 10 may be used for treating different types of teeth misalignment or malocclusion, including but not limited to one or more of: closing gaps ("space closure"), creating/widening gaps, tooth rotation, tooth intrusion/extrusion, and tooth translation, to name a few. It should further be noted that in certain non-limiting embodiments of the present technology, applying the aligner 10 to the upper teeth 16 may further include applying specific attachments (also known as "fixing blocks") thereto.

As it may become apparent, the aligner 10 may be designed in such a way that its current configuration is representative of a desired position of the upper teeth 16 at a given stage of the orthodontic treatment, which thus allows, due to stiffness properties of the material of the aligner 10, imposing a respective force onto each crown portion of a respective one of the upper teeth 16 appointed for the orthodontic treatment.

Thus, referring back to FIG. 1, in order to cause the given tooth 15 to reach the aligned position, first, various configurations of the aligner 10 may be used to move each one of the upper teeth 16 before the given tooth 15 posteriorly (backwards), thereby preparing space for the given tooth 15 to be further moved inwardly. Second, the aligner 10 may be configured to cause the given tooth 15 to move inwardly, towards the aligned position thereof within the upper teeth 16. More specifically, the aligner 10 can be configured to cause the given tooth 15 to move (i) translationally in a labial direction; and (ii) rotationally counterclockwise around its tooth axis, until the given tooth 15 reaches the aligned position within the upper teeth 16.

In accordance with the non-limiting embodiments of the present technology, a size, a form factor (such as a U-shape or a V-shape, for example), and a configuration of the aligner 10, including a material and a thickness thereof, depend generally on a particular malocclusion disorder of the subject (such as the misalignment of the given tooth 15 within the upper teeth 16), at which the orthodontic treatment is aimed. However, as an example, in some non-limiting embodiments of the present technology, the thickness of the aligner 10 may be about 0.7 mm. In other non-limiting embodiments of the present technology, the thickness is selected from 0.7 mm, 0.75 mm, 0.8 mm, 0.85 mm, 0.9 mm, 0.95 mm, and 1.0 mm. In yet other non-limiting embodiments of the present technology, the aligner 10 may have regions of variable thickness, such as in interdental regions 24, as an example.

According to certain non-limiting embodiments of the present technology, the aligner 10 may be made of a polymer, such as a thermoplastic material. In other non-limiting embodiments of the present technology, the aligner 10 may be made of poly-vinyl chloride (PVC). In yet other non-limiting embodiments of the present technology, the aligner 10 may be made of polyethylene terephthalate glycol (PETG). Other suitable materials can also be used to form the aligner 10.

In some non-limiting embodiments of the present technology, the aligner 10 may be manufactured using additive manufacturing techniques, such as 3D printing techniques where the aligner 10 is formed according to a pre-generated 3D digital model thereof.

In other non-limiting embodiments of the present technology, the aligner 10 may be produced by a thermoforming process where (1) an unfinished aligner is produced, using a preform, on a respective aligner mold (not depicted) associated with a respective stage of the orthodontic treatment, which is configured to shape the inner surface 22 of the aligner 10; and (2) the unfinished aligner is cut along a predetermined cut line to remove excess material therefrom, thereby producing the aligner 10, the predetermined cut line defining the at least one edge of the channel 18 of the aligner 10.

In specific non-limiting embodiments of the present technology, the aligner 10 may be manufactured in accordance with one or more methods described in a co-owned U.S. Pat. No. 11,191,618-B1, issued on Dec. 7, 2021, and entitled "SYSTEMS AND METHODS FOR FORMING A DENTAL APPLIANCE," the content of which is incorporated herein by reference in its entirety.

Figure 7:
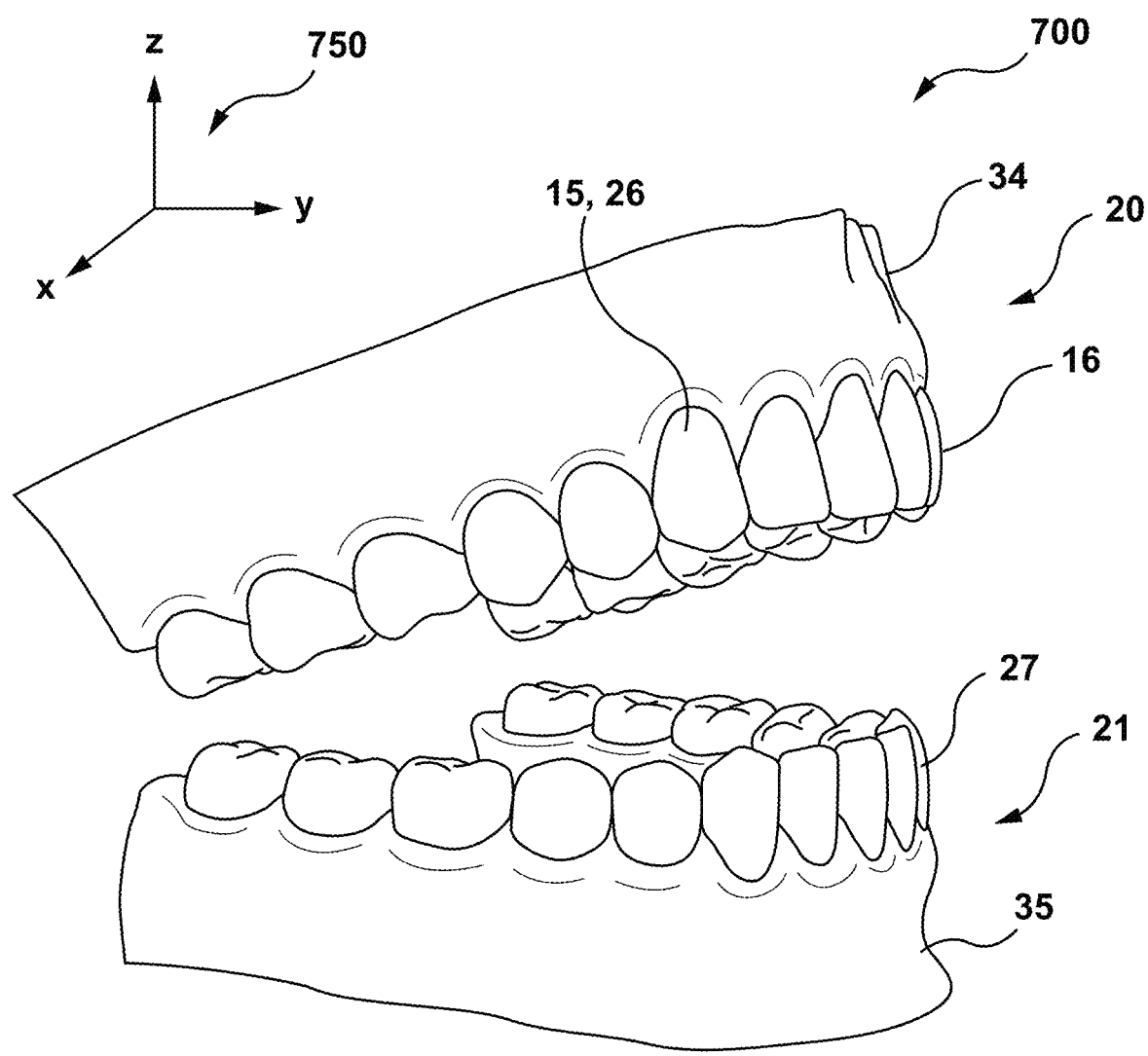
FIG. 7 depicts a perspective view of a 3D digital model of the upper and lower arch forms of FIG. 1, in accordance with the non-limiting embodiments of the present technology.

Needles to say that, although in the depicted embodiments of FIGS. 2A and 2B, the aligner 10 is configured to be applied onto the upper teeth 16, in other non-limiting embodiments of the present technology, a certain configuration of the aligner 10 may be applied to teeth of a lower arch form (such as a lower arch form 21, 3D representation of which is depicted in FIG. 7) of the subject aimed at respective malocclusion disorders.

In sum, based on the target position of the given tooth 15, such as that associated with the alignment thereof within the upper teeth 16, a planned tooth movement can be determined, as described above, thereby defining a planned tooth trajectory of the given tooth 15 from the initial position, as depicted in FIG. 1, to the target position thereof. Further, based on the so planned movement of the given tooth 15, the respective force to be applied thereto to cause the given tooth 15 to move along the planned tooth trajectory can be determined. Further, based on the respective force, at least one configuration of the aligner 10, configured to exert such a force, can be determined. As mentioned above, the at least one configuration of the aligner 10, in accordance with certain non-limiting embodiments of the present technology, can include, without limitation, a thickness of the aligner 10, elasticity properties of the material of the aligner 10, use of additional attachments for the given tooth 15, and the like.

How the respective force to be applied to the given tooth 15 can be determined based on the nature of the planned movement thereof, will now be described.

Figure 3A:
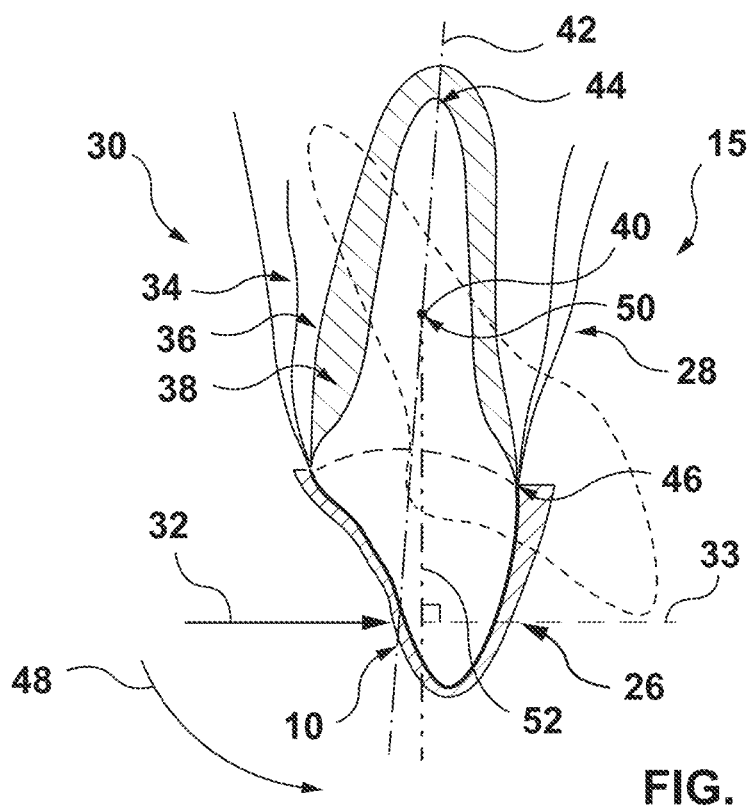
FIGS. 3A to 3D depict schematic diagrams of example tooth movements of a given tooth of the subject's teeth of FIG. 1, in accordance with certain embodiments of the present technology.

With reference to FIG. 3A, there is depicted a schematic diagram of a distal view of the given tooth 15 illustrating a first example of a tooth movement thereof under a force 32 applied by the aligner 10, in accordance with certain non-limiting embodiments of the present technology.

As it can be appreciated, the given tooth 15 includes a crown portion 26 and a root portion 28. Tissues of a periodontium 30 surrounding and supporting the upper teeth 16, and the given tooth 15, in particular, include the upper gingiva 34, an alveolar bone 36, and a periodontal ligament 38. The periodontal ligament 38 surrounds the root portion 28 and attaches the given tooth 15 to the alveolar bone 36. Thus, it can be said that the given tooth 15 is restrained in the alveolar bone 36 by forces (not separately depicted) from the periodontal ligament 38 and the neighboring ones of the upper teeth 16, such as the first and second adjacent teeth 13, 17, depicted in FIG. 1.

Accordingly, to cause the planned tooth movement of the given tooth 15, the force 32 should be applied to the given tooth 15 (to the crown portion 26 thereof), such as via the aligner 10, causing the periodontal ligament 38 to deform in a respective desired direction, towards the target position. It should be expressly understood that the force 32 is depicted in FIG. 3A as a single force only for the sake of clarity of the present description and may comprise a superposition of a system of forces applied to the given tooth 15 by the aligner 10 as well as by other components (not separately depicted) applied with the aligner 10, such as elastics, attachments, and the like.

Further, the force 32, when applied to the crown portion 26, may create a torque 48. Accordingly, such an application of the force 32 may cause the given tooth 15 to move (1) translationally; and (2) rotationally around a center of rotation 50. It should be noted that, akin to the force 32, the torque 48 may be a resultant force torque of a torque system influencing the given tooth 15 caused by the force 32. In this regard, the torque 48 may be determined in accordance with the following equation:

$$T = F \times D, \quad (1)$$

where
  T is the torque 48,
  F is the force 32, and
  D is a distance 52, over a perpendicular, between a center of resistance (CR) point 40 and a line of action 33 of the force 32.

In the context of the present specification, the term "CR point" of a given body denotes a point, at which imposing a given mechanical force results in a translational movement (or otherwise, a bodily movement) of the given body in a direction of the given mechanical force, along a line of action thereof. As used herein, the CR point 40 is mostly determined for restrained bodies, such as teeth (for example, the given tooth 15), and, in a sense, may be considered as an equivalent to a center of gravity point (center of mass point) for unrestrained (free) bodies. For example, it may be shown that in certain subjects the CR point 40 can be determined to be located on a tooth axis 42 of the given tooth 15, at a length from 24 to 35% of a length of the root portion 28 apically (towards an apex 44 of the given tooth 15) from an alveolar crest 46 of the alveolar bone 36.

Practically speaking, a particular tooth movement of the given tooth 15 may be projected by varying a torque-to-force ratio T:F between the torque 48 and the force 32. To that end, as it can be appreciated from Equation (1), after applying the force 32 of a given magnitude, a magnitude of the torque 48 may be varied by varying the distance 52 from the line of action 33 to the CR point 40. Thus, the longer the distance 52 is, the higher is the torque-to-force ratio T:F.

Thus, in one non-limiting example, in certain subjects, when the ratio T:F is 0:1, the given tooth 15 will move purely rotationally with the center of rotation 50 substantially coinciding with the CR point 40. To that end, the crown portion 26 will be moving labially (buccally) and the apex 44 will be moving lingually. Such a movement can also be referred to as an uncontrolled tipping tooth movement.

Figure 3B:
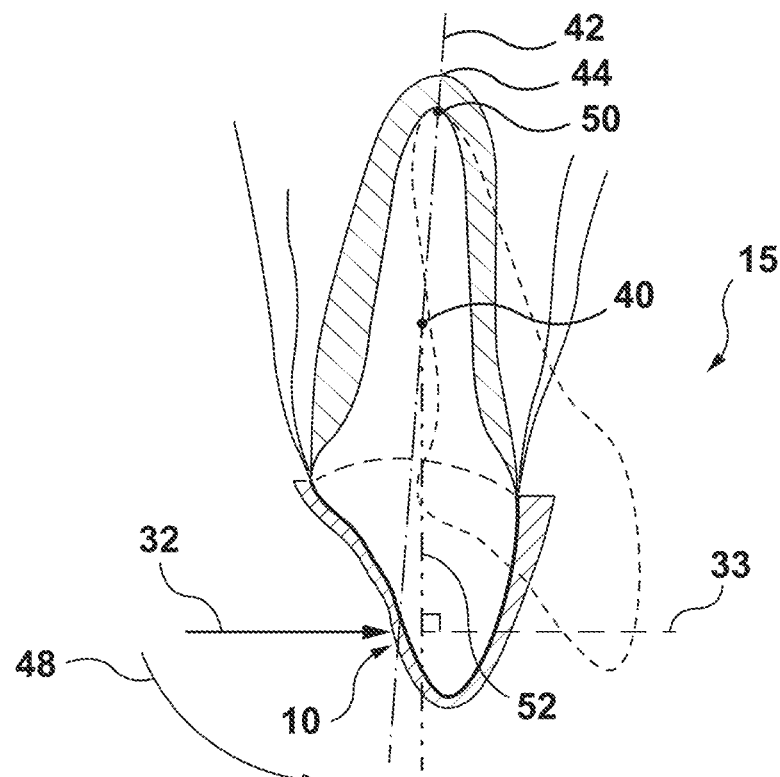

With reference to FIG. 3B, there is depicted a schematic diagram of the distal view of the given tooth 15 illustrating a second example of the tooth movement of the given tooth 15 modelled under the force 32, in accordance with some non-limiting embodiments of the present technology.

In the depicted embodiments of FIG. 3B, the torque-to-force ratio T:F is between 5:1 and 7:1, which causes the center of rotation 50 to shift towards the apex 44, in certain subjects. To that end, the force 32 causes the given tooth 15 to move as a "pendulum" around the apex 44. By varying the ratio T:F within a predetermined range, it is possible to produce similar movements of the given tooth 15 based on respective locations of the center of rotation 50 near the apex 44, each of these tooth movements can be referred to as a controlled tipping tooth movement.

Figure 3C:
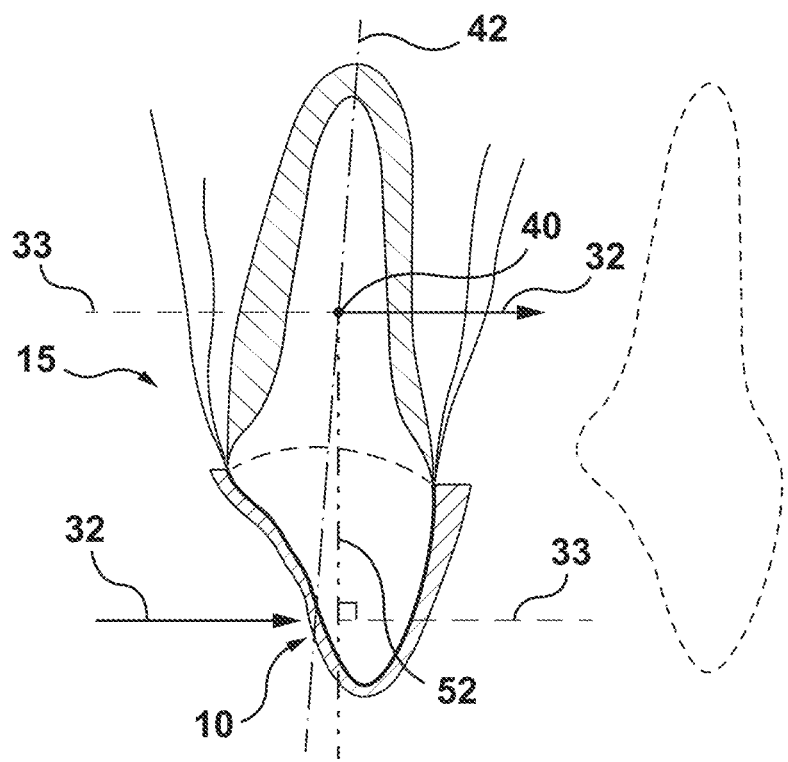

With reference to FIG. 3C, there is depicted a schematic diagram of the distal view of the given tooth 15 illustrating a third example of the tooth movement of the given tooth 15 under the force 32, in accordance with some non-limiting embodiments of the present technology.

In the depicted embodiments of FIG. 3C, the torque-to-force ratio T:F is around 10:1, which causes the center of rotation 50 to shift to infinity. Accordingly, with such a value of the torque-to-force ratio T:F, the torque 48 can be said to cause the line of action 33 of the force 32 to extend through the CR point 40, thereby causing the given tooth 15, in certain subjects, to move purely translationally therealong. Such movements can also be referred to as bodily tooth movements.

Some non-limiting examples of the bodily tooth movements of the given tooth 15 may also include an extrusion tooth movement and an intrusion tooth movement (not separately depicted) where the force 32 is directed along the tooth axis 42 through the CR point 40 downwards or upwards, respectively.

Figure 3D:
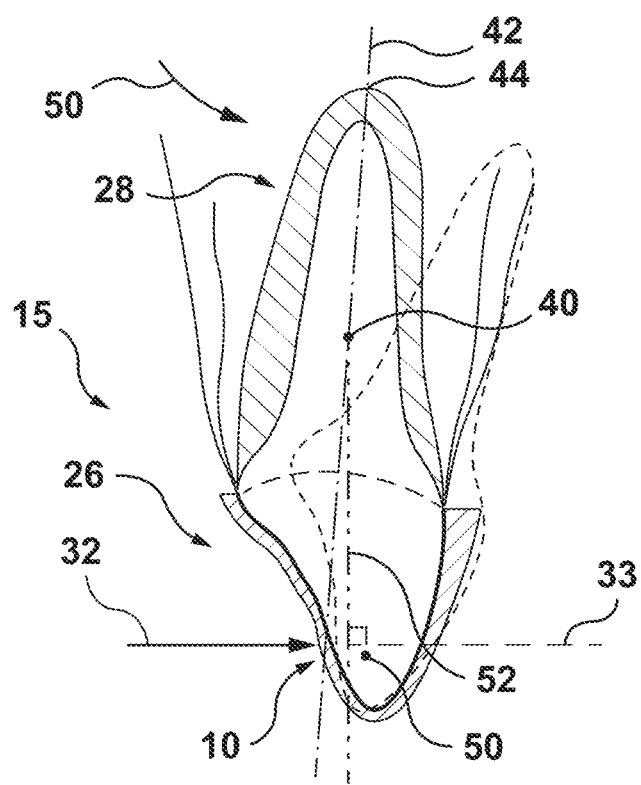

Further, with reference to FIG. 3D, there is depicted a schematic diagram of the distal view of the given tooth 15 performing a fourth example of the tooth movement under the force 32, in accordance with some non-limiting embodiments of the present technology.

As it can be appreciated, when the torque-to-force ratio T:F is further increased to values such as 14:1, for example, the center or rotation 50 may be shifted to the crown portion 26, thereby causing the given tooth 15 to rotate around the crown portion 26. To that end, the apex 44 of the root portion 28 moves buccally, which can be referred to as a root uprighting tooth movement.

Also, it should be expressly understood that the above examples of the tooth movement of the given tooth are not an exhaustive list; and depending on a configuration of the force 32 and an application point thereof to the crown portion 26, other tooth movement examples of the given tooth 15 can be caused. For example, applying a force couple to the crown portion 26 can cause an axial rotation to the given tooth 15 around the tooth axis 42. Also, it should be expressly understood that the above example tooth movements can be executed in both labiolingual and mesiodistal directions associated with the given tooth 15.

Thus, based on the planned tooth movement, the respective magnitudes of the force 32 and the torque 48 can be determined, as can further be the respective configuration of the aligner 10 configured to exert the force 32 and the torque 48 of the so determined magnitudes onto the given tooth 15. Further, the so determined configuration of the aligner 10, along with an indication of the planned tooth trajectory for the given tooth 15, defined by the planned tooth movement, can be added to an orthodontic treatment plan for the given tooth 15.

Figure 4:
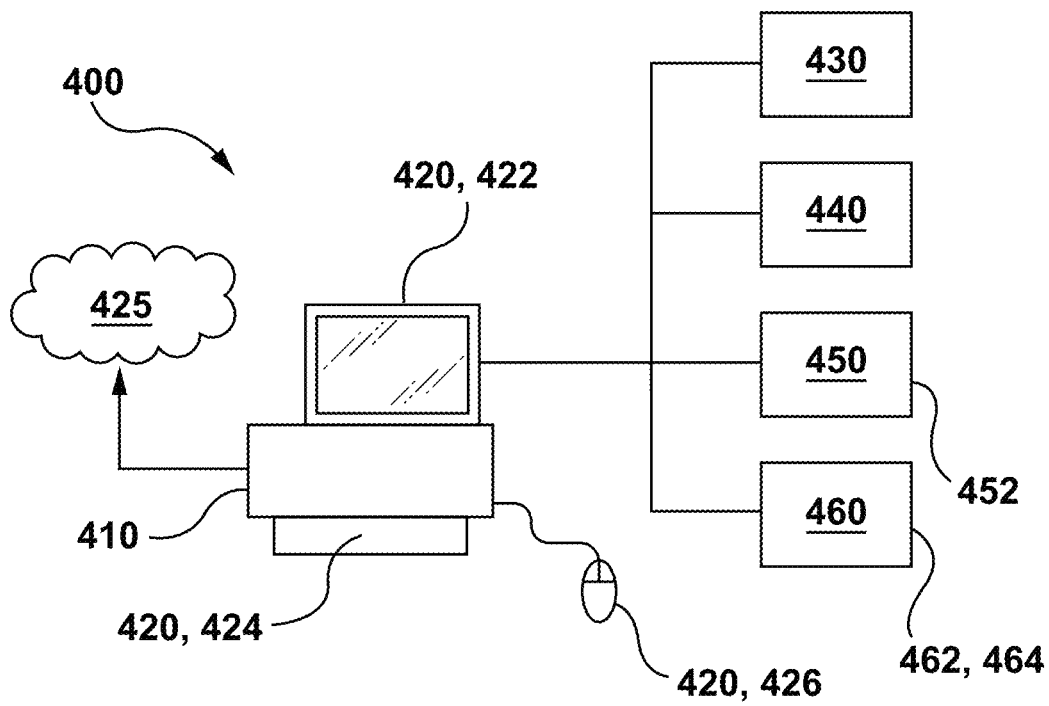
FIG. 4 depicts a schematic diagram of a system for determining an orthodontic treatment for the subject of FIG. 1 based on modelling some of the tooth movements of the given tooth, examples of which are depicted in FIGS. 3A to 3D, in accordance with certain embodiments of the present technology.
Figure 5:
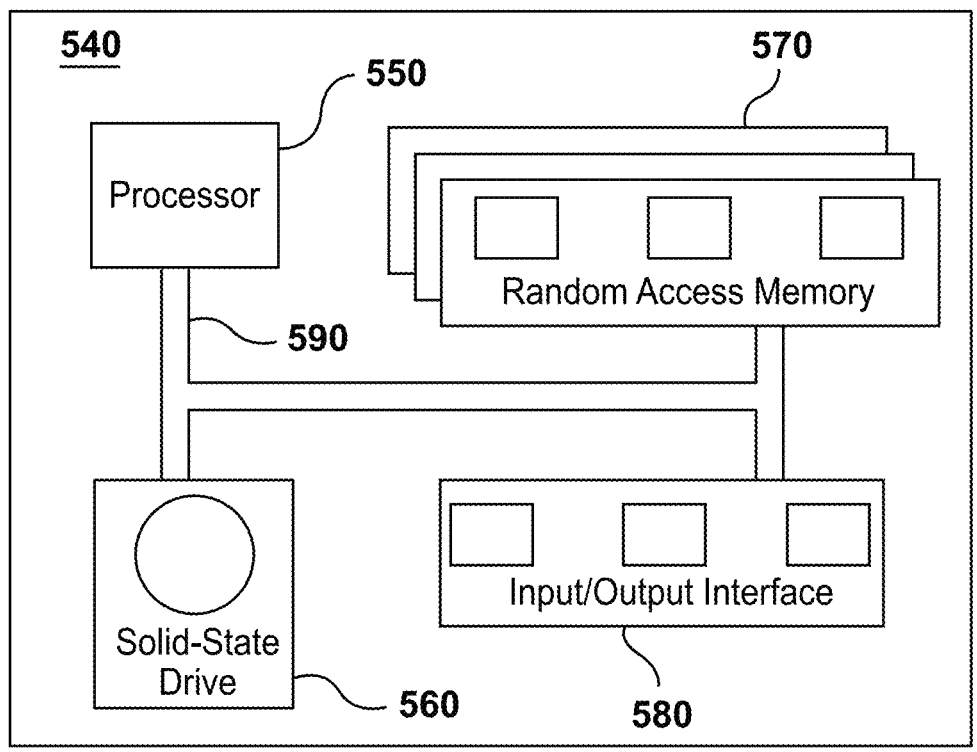
FIG. 5 depicts a schematic diagram of a computing environment of the system of FIG. 4, in accordance with certain embodiments of the present technology.

However, as mentioned above, in some non-limiting embodiments of the present technology, the tooth movement of the given tooth 15 from the initial to the target position thereof may include a combination of the above-mentioned example tooth movements, which are also collectively referred to herein as a "plurality of tooth movement components". More specifically, returning to the example of FIG. 1, the tooth movement of the given tooth 15 can include, first, a counterclockwise axial rotation (not depicted) around the tooth axis 42; and further a translation (depicted in FIG. 5) in the lingual direction, between the first and second adjacent teeth 13, 17. Additionally, the tooth movement of the given tooth 15 may include an extrusion (not depicted) thereof from the upper gingiva 34. In another example (not depicted), the tooth movement can include the controlled tipping, as depicted in FIG. 4, and extrusion (not depicted). In yet another example (also not depicted), the tooth movement can include the translation, as depicted in FIG. 5, the axial rotation (not depicted) around the tooth axis 42, and the controlled tipping, as depicted in FIG. 4.

As it can be appreciated, the plurality of tooth movement components is indicative of possible degrees of freedom of the given tooth 15 within the alveolar bone 36, as a given tooth movement component corresponds to a respective single coordinate, linear or angular, along which the tooth movement of the given tooth 15 is feasible.

Further, conventional approaches to modelling such complex tooth movements for determining the respective magnitudes of the force 32 and the torque 48 include a modelling of the given tooth 15 performing at least some of these tooth movements components simultaneously at a given movement in time. This further may result in determining the force 32 comprising a complex force system to be applied to the given tooth 15, which would be challenging to accurately apply using the respective configuration of the aligner 10. Thus, such an "aggregate" approach to considering the plurality of tooth movement components mentioned above may lead to an elevated risk of a deviation of an actual tooth trajectory of the given tooth 15, caused by applying the respective configuration of the aligner 10, from the planned one. As it can be appreciated, such deviations from the orthodontic treatment plan may further result in the given tooth 15 colliding with one of the neighboring and/or opposing teeth. Also, the complex force systems applied to the given tooth 15 through the respective configuration of the aligner 10 can cause additional discomfort to the subject, as it would include deforming the periodontal ligament 38 of the given tooth 15 in multiple directions at the given moment in time.

Also, for resolving some misalignments, dividing the tooth movements of the teeth in the respective tooth movement components can be required for further sequential application thereof. For example, in cases of crowding of the subject's teeth, such as depicted in FIG. 1, those of the upper teeth 16 located distally to the given tooth 15 need to be moved posteriorly (backwards), prior to causing the given tooth 15 to move inwardly between the first and second adjacent teeth 13, 17. On the other hand, the given tooth 15, before having the space to move inwardly, can be caused to move rotationally around the tooth axis 42.

Thus, the developers of the present technology have appreciated that modelling and further causing each of the plurality of tooth movement components separately may allow minimizing deviations between the planned and actual tooth trajectories. More specifically, the developers have devised methods and systems for determining the orthodontic treatment plan including (i) identifying, within the planned tooth movement, the plurality of tooth movement components; and (ii) determining, for each one of the plurality of tooth movement components, a respective magnitude value indicative of a path length at which the given tooth 15 is to displace performing the given one of the plurality of tooth movement components, thereby defining portions of the planned tooth trajectory. By doing so, the present methods are directed to determining the planned tooth trajectory having simpler portions thereof, corresponding to respective ones of the plurality of tooth movements, which may allow for a more accurate reproduction thereof under the respective configuration of the aligner 10.

Accordingly, such an approach to modelling and further causing the tooth movement of the given tooth 15 may allow for one or both of: (i) a better reliability of the so determined orthodontic treatment plan, minimizing the risks of collisions of the given tooth 15 with other teeth; and (ii) an increased wear comfort of the resulting configuration of the aligner 10, hence increasing the overall efficacy of the orthodontic treatment.

Also, in certain non-limiting embodiments of the present technology, as the tooth movement components are separate, the order, speed and duration can be tailored for a desired effect. For example, tooth movement components can be ordered in such a way as to further increase an effectiveness of the orthodontic treatment. As another example, each of the tooth movement components can be assigned a desired speed value of execution to balance treatment time and safety.

How the orthodontic treatment plan can be determined, in accordance with certain non-limiting embodiments of the present technology, will be described below with reference to FIGS. 6 to 10.

System

With reference to FIGS. 4 and 5, there is depicted a schematic diagram of a system 400 suitable for determining the orthodontic treatment, in accordance with certain non-limiting embodiments of the present technology.

It is to be expressly understood that the system 400 as depicted is merely an illustrative implementation of the present technology. Thus, the description thereof that follows is intended to be only a description of illustrative examples of the present technology. This description is not intended to define the scope or set forth the bounds of the present technology. In some cases, what is believed to be helpful examples of modifications to the system 400 may also be set forth below. This is done merely as an aid to understanding, and, again, not to define the scope or set forth the bounds of the present technology. These modifications are not an exhaustive list, and, as a person skilled in the art would understand, other modifications are likely possible. Further, where this has not been done (i.e., where no examples of modifications have been set forth), it should not be interpreted that no modifications are possible and/or that what is described is the sole manner of implementing that element of the present technology. As a person skilled in the art would understand, this is likely not the case. In addition, it is to be understood that the system 400 may provide in certain instances simple implementations of the present technology, and that where such is the case they have been presented in this manner as an aid to understanding. As persons skilled in the art would further understand, various implementations of the present technology may be of a greater complexity.

In certain non-limiting embodiments of the present technology, the system 400 of FIG. 4 comprises a computer system 410. The computer system 410 may be configured, by pre-stored program instructions, to determine, based on image data associated with the subject, such as a 3D digital model of the upper arch form 20, a tooth trajectory for the given tooth 15 for further use in developing an orthodontic treatment of the subject. In additional non-limiting embodiments of the present technology, the computer system 410 may further be configured to produce at least one configuration of the aligner 10, causing the given tooth 15 to move along the so determined tooth trajectory in the course of the orthodontic treatment.

To that end, in some non-limiting embodiments of the present technology, the computer system 410 may be configured to receive image data pertaining to the subject or to a given stage of the orthodontic treatment. According to some non-limiting embodiments of the present technology, the computer system 410 may receive the image data via local input/output interface (such as USB, as an example, not separately depicted). In other non-limiting embodiments of the present technology, the computer system 410 may be configured to receive the image data over a communication network 425, to which the computer system 410 is communicatively coupled.

In some non-limiting embodiments of the present technology, the communication network 425 is the Internet and/or an Intranet. Multiple embodiments of the communication network may be envisioned and will become apparent to the person skilled in the art of the present technology. Further, how a communication link between the computer system 410 and the communication network 425 is implemented will depend, inter alia, on how the computer system 410 is implemented, and may include, but is not limited to, a wire-based communication link and a wireless communication link (such as a Wi-Fi communication network link, a 3G/4G communication network link, and the like).

It should be noted that the computer system 410 can be configured for receiving the image data from a vast range of devices. Some of such devices can be used for capturing and/or processing data pertaining to maxillofacial and/or cranial anatomy of the subject. In certain embodiments, the image data received from such devices is indicative of properties of anatomical structures of the subject, including: teeth, intraoral mucosa, maxilla, mandible, temporomandibular joint, and nerve pathways, among other structures. In some non-limiting embodiments of the present technology, at least some of the image data is indicative of properties of external portions of the anatomical structures, for example dimensions of a gingival sulcus, and dimensions of an external portion of the given tooth 15 of the upper teeth 16, such as the crown portion 26 thereof extending outwardly of the gingival sulcus. In some embodiments, the image data is indicative of properties of internal portions of the anatomical structures, for example, volumetric properties of bone surrounding an internal portion of the given tooth 15 extending inwardly of the gingival sulcus, such as the root portion 28 of the given tooth 15. Under certain circumstances, such volumetric properties may be indicative of periodontal anomalies which may be factored into an orthodontic treatment plan. In some non-limiting embodiments of the present technology, the image data includes cephalometric image datasets. In some embodiments, the image data includes datasets generally intended for the practice of endodontics. In some embodiments, the image data includes datasets generally intended for the practice of periodontics.

In alternative non-limiting embodiments of the present technology, the computer system 410 may be configured to receive the image data associated with the subject directly from an imaging device 430 communicatively coupled thereto. Broadly speaking, the processor 550 may be configured to cause the imaging device 430 to capture and/or process the image data of the lower teeth 27 and the periodontium (not depicted) of the subject. In certain non-limiting embodiments of the present technology, the image data may include, for example, one or more of: (1) images of external surfaces of respective crown portions of the upper teeth 16, such as the crown portion 26 of the given tooth 15, (2) images of an external surface of the periodontium including those of the upper gingiva 34, the alveolar bone 36, the periodontal ligament 38, and images of superficial blood vessels and nerve pathways associated with the upper teeth 16; and (3) images of an oral region. By doing so, the imaging device 430 may be configured, for example, to capture image data of the upper arch form 20 of the subject. In another example, the imaging device may also be configured to capture and/or process image data of the lower arch form (such as a lower arch form 21 depicted in FIG. 7) associated with the subject without departing from the scope of the present technology. It should be noted that the image data may include two-dimensional (2D) data and/or three-dimensional data (3D). Further, in certain non-limiting embodiments of the present technology, the image data includes 2D data, from which 3D data may be derived, and vice versa.

In some non-limiting embodiments of the present technology, the imaging device 430 may comprise an intra-oral scanner enabling to capture direct optical impressions of the upper arch form 20 the subject.

In a specific non-limiting example, the intraoral scanner can be of one of the types available from MEDIT, CORP. of 23 Goryeodae-ro 22-gil, Seongbuk-gu, Seoul, South Korea. It should be expressly understood that the intraoral scanner can be implemented in any other suitable equipment.

In yet other non-limiting embodiments of the present technology, the imaging device 430 can comprise a 3D laser scanner enabling to obtain a respective point cloud 3D digital model of the upper arch form 20—such as by scanning the upper arch form 20 directly or a mold thereof and thus registering three-dimensional coordinates of points representative of the surface of the upper arch form 20.

In a specific non-limiting example, the 3D laser scanner can be of one of the types available from LASER DESIGN LTD. of 5900 Golden Hills Drive, Minneapolis, Minn. 55416. It should be expressly understood that the desktop scanner can be implemented in any other suitable equipment.

Further, it is contemplated that the computer system 410 may be configured for processing of the received image data. The resulting image data of each one of the upper arch form 20 and the lower arch form 21 received by the computer system 410 is typically structured as a binary file or an ASCII file, may be discretized in various ways (e.g., point clouds, polygonal meshes, pixels, voxels, implicitly defined geometric shapes), and may be formatted in a vast range of file formats (e.g., STL, OBJ, PLY, DICOM, and various software-specific, proprietary formats). Any image data file format is included within the scope of the present technology. For implementing functions described above, the computer system 410 may further comprise a corresponding computing environment.

Further, in some non-limiting embodiments of the present technology, the system 400 may be configured, based on the 3D digital model of the upper arch form 20, for example, determine the orthodontic treatment for the subject including (i) determining tooth trajectories for the at least some of the upper teeth 16, such as the given tooth 15, defining their paths from their initial to target positions; and (ii) respective forces to be applied to the at least some of the upper teeth 16 causing them to move along the so determined tooth trajectories. How the orthodontic treatment can be determined, in accordance with certain non-limiting embodiments of the present technology, will be described in detail below with reference to FIGS. 6 to 10.

Further, in certain non-limiting embodiments of the present technology, the system 400 may be configured to produce at least one configuration of the aligner 10 based on the planned orthodontic treatment as mentioned above. To that end, the system 400 can further include a manufacturing system 440, to which the processor 550 can be configured to send respective instructions causing the manufacturing system 440 to produce the at least one configuration of the aligner 10. In some non-limiting embodiments of the present technology, the manufacturing system 440 can be a thermoforming system configured to produce an unfinished aligner (not depicted), for example, using a thermopriming process, in which a preform aligner (not depicted) is shaped on the mold of the upper arch form 20.

In a specific non-limiting example, the thermoforming system can be of one of the types provided by HAMER LTD. of Rambla Antoni Gaudi, 108792 La Granada (Barcelona) Spain. It should be expressly understood that the thermoforming system can be implemented in any other suitable equipment.

Further, after the thermoforming the unfinished aligner, the system 400 can be configured to trim excess material thereof along a cut line to produce an edge of the aligner 10.

To that end, in some non-limiting embodiments of the present technology, the system 400 can be configured to determine (or otherwise receive) data indicative of the cut line and mark the cut line on the unfinished aligner. To that end, the system 400 may further comprise a marking subsystem 450. It is not limited how the marking subsystem 450 may be implemented; however, in various non-limiting embodiments of the present technology, the marking subsystem 450 may include a marking head 452 for applying the cut line onto the unfinished aligner and a first robotic arm (not depicted) for holding and manipulating the unfinished aligner (not depicted) around the marking head 452. In some non-limiting embodiments of the present technology, the marking head 452 may further comprise a coloring material storage (not depicted) for storing a coloring material (such as ink, as an example) and a supply control block (not depicted). In some non-limiting embodiments of the present technology, the marking head 452 may be implemented as a laser apparatus configurable to scorch the cut line (not depicted) on the unfinished aligner (not depicted).

In certain non-limiting embodiments of the present technology, the system 400 may further be configured to detect the cut line applied on the unfinished aligner and cut along the cut line to produce the aligner 10. In this regard, the system 400 may further comprise a forming subsystem 460. In some non-limiting embodiments of the present technology, the forming subsystem 460 may include a second robotic arm (not depicted), at an end-effector of which there is installed a camera device 462. In some non-limiting embodiments of the present technology, the camera device 462 can be any appropriate digital camera configured to detect the cut line applied by the marking subsystem 450 described above onto the unfinished aligner, including, for example, but not limited to, a coupled-charged device camera (a CCD camera). Further, as mentioned above, the forming subsystem 460 may include the cutting device 464. Non limiting examples of the cutting device 464 may include a laser-based cutting device, a mechanical cutting device such as using a blade with a rotary or linear cutting action, and a waterjet-based cutting device, as an example.

In some non-limiting embodiments of the present technology, both the marking subsystem 450 and the forming subsystem 460 of the system 400 may be implemented as described in a co-owned U.S. patent application Ser. No. 16/704,718 filed on Dec. 5, 2019, entitled "SYSTEMS AND METHODS FOR FORMING PERSONALIZED DENTAL APPLIANCES", the content of which is hereby incorporated by reference in its entirety.

Thus, the forming subsystem 460 may be configured to: (1) cause the camera device 462 to move around the unfinished aligner (not depicted) with the cut line (not depicted) applied thereon to detect the cut line and generating respective image data thereof; (2) receive the image data of the cut line; and (3) based on the received image data of the cut line, cause cutting, by the cutting device 464 the unfinished aligner along the cut line, thereby forming the aligner 10.

In other non-limiting embodiments of the present technology, the forming subsystem 460 may be configured for cutting the unfinished aligner without requiring detection of the cut line. Instead, the determined cut line is used to guide the cutting—for example, based on received data indicative of a position of the cut line within the unfinished aligner. In some non-limiting embodiments of the present technology, the data indicative of the position of the cut line within the unfinished aligner may include at least one of: Cartesian coordinates; angular data indicative of a cutting angle for cutting the unfinished aligner; and a distance from the cutting device 464, as an example.

However, in other non-limiting embodiments of the present technology, the manufacturing system 440 can comprise an additive manufacturing system, such as a 3D printer, configured for direct manufacturing (printing) the at least one configuration of the aligner 10.

In a specific non-limiting example, the 3D printer can be of one of the types of HP Jet Fusion available from HP INC. of 1501 Page Mill Road, Palo Alto, Calif., 94304, United States of America. It should be expressly understood that the 3D printer can be implemented in any other suitable equipment.

Further, with reference to FIG. 5, there is depicted a schematic diagram of a computing environment 540 suitable for use with some implementations of the present technology. The computing environment 540 comprises various hardware components including one or more single or multi-core processors collectively represented by the processor 550, a solid-state drive 560, a random-access memory 570 and an input/output interface 580. Communication between the various components of the computing environment 540 may be enabled by one or more internal and/or external buses 590 (for example, a PCI bus, universal serial bus, IEEE 1394 "Firewire" bus, SCSI bus, Serial-ATA bus, ARINC bus, etc.), to which the various hardware components are electronically coupled.

The input/output interface 580 allows enabling networking capabilities such as wire or wireless access. As an example, the input/output interface 580 comprises a networking interface such as, but not limited to, a network port, a network socket, a network interface controller, and the like. Multiple examples of how the networking interface may be implemented will become apparent to the person skilled in the art of the present technology. For example, but without being limiting, the input/output interface 580 may implement specific physical layer and data link layer standard such as Ethernet™, Fibre Channel, Wi-Fi™ or Token Ring™. The specific physical layer and the data link layer may provide a base for a full network protocol stack, allowing communication among small groups of computers on the same local area network (LAN) and large-scale network communications through routable protocols, such as IP.

According to implementations of the present technology, the solid-state drive 560 stores program instructions suitable for being loaded into the random-access memory 570 and executed by the processor 550, according to certain aspects and embodiments of the present technology. For example, the program instructions may be part of a library or an application.

In some non-limiting embodiments of the present technology, the computing environment 540 is implemented in a generic computer system, which is a conventional computer (that is, an "off the shelf" generic computer system). The generic computer system may be a desktop computer/personal computer but may also be any other type of electronic device such as, but not limited to, a laptop, a mobile device, a smart phone, a tablet device, or a server.

As persons skilled in the art of the present technology may appreciate, multiple variations as to how the computing environment 540 can be implemented may be envisioned without departing from the scope of the present technology.

Referring back to FIG. 4, the computer system 410 has at least one interface device 420 for providing an input or an output to a user of the system 400, the interface device 420 being in communication with the input/output interface 580. In the embodiment of FIG. 4, the interface device is a screen 422. In other non-limiting embodiments of the present technology, the interface device 420 may be a monitor, a speaker, a printer, or any other device for providing an output in any form such as an image form, a written form, a printed form, a verbal form, a 3D model form, or the like.

In the depicted embodiments of FIG. 4, the interface device 420 also comprises a keyboard 424 and a mouse 426 for receiving input from the user of the system 400. Other interface devices 420 for providing an input to the computer system 410 can include, without limitation, a USB port, a microphone, a camera, or the like.

The computer system 410 may be connected to other users, such as through their respective clinics, through a server (not depicted). The computer system 410 may also be connected to stock management or client software which could be updated with stock when the orthodontic treatment has been determined and/or schedule appointments or follow-ups with clients, for example.

Figure 6:
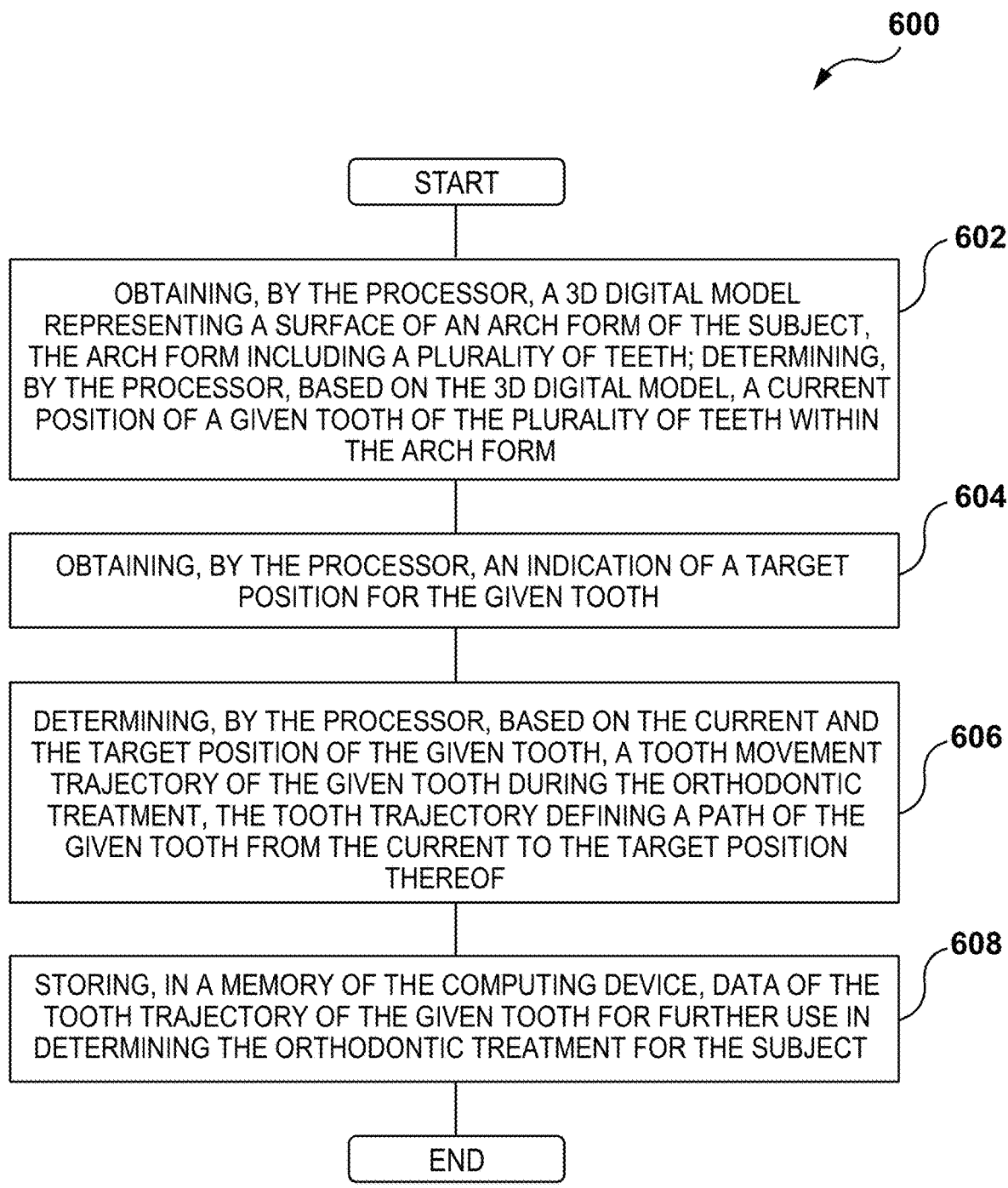
FIG. 6 depicts a flowchart of a method for determining the orthodontic treatment for the subject of FIG. 1, in accordance with certain embodiments of the present technology.

Thus, given the architecture and examples provided above, it is now possible to execute a method of determining the orthodontic treatment for the subject, such as that including application of the aligner 10 to cause the given tooth 15 to move to the target position, as described above. With reference to FIG. 6, there is depicted a schematic diagram of a method 600, in accordance with certain non-limiting of the present technology. For example, the method 600 can be executed by the processor 550 of the system 400.

Method

Step 602: Obtaining, by the Processor, a 3D Digital Model Representing a Surface of an Arch Form of the Subject, the Arch Form Including a Plurality of Teeth; Determining, by the Processor, Based on the 3D Digital Model, a Current Position of a Given Tooth of the Plurality of Teeth within the Arch Form The method 600 commences at step 602 with the processor 550 being configured to obtain the image data associated with the subject. More specifically, according to certain non-limiting embodiments of the present technology, the processor 550 can be configured to receive the 3D digital models of the arch forms of the subject.

With reference to FIG. 7, there is schematically depicted a perspective view of a 3D digital model 700 representing current configurations of the arch forms of the subject, which can be used, by the processor 550 for determining the orthodontic treatment, in accordance with certain non-limiting embodiments of the present technology.

As noted above, according to the non-limiting embodiments of the present technology, the upper arch form 11 comprises the upper teeth 16 (also referred to herein as "maxillary teeth") and the upper gingiva 34; and the lower arch form 21 comprises lower teeth 27 (also referred to herein as "mandibular teeth") and a lower gingiva 35. As it can be appreciated, each one of the upper and lower teeth 16, 27 are represented, in the 3D model 700, by respective crown portions thereof. However, in other non-limiting embodiments of the present technology, the upper and lower teeth 16, 27 can further be represented by their root portions (not depicted) in the 3D digital model 700.

In some non-limiting embodiments of the present technology, the processor 550 can be configured to receive, from the imaging device 430 communicatively coupled with the processor 550, the 3D digital model 700 comprising a respective plurality of mesh elements (not depicted) representative of respective surfaces of the upper and lower arch forms 20, 21. For example, the imaging device 430 can be configured to generate the plurality of mesh elements including, without limitation, triangular mesh elements, quadrilateral mesh elements, convex polygonal mesh elements, or even concave polygonal mesh elements, as an example, without departing from the scope of the present technology.

However, in those embodiments where the imaging device 430 is the 3D laser scanner, the 3D digital model 700 comprises a 3D point cloud representative of the surfaces of the upper and lower arch forms 20, 21.

Also, in some non-limiting embodiments of the present technology, the processor 550 can be configured to obtain the 3D digital model 700 including independently generated 3D digital models of each one of the upper and lower arch forms 20, 21, not representing the current bite position of the subject. To that end, according to certain non-limiting embodiments of the present technology, the processor 550 can be configured to model, using the 3D digital model 700, the current bite position between the upper and lower arch forms 20, 21, which is indicative of a current occlusion between the upper and lower teeth 16, 27. It is not limited how the processor 550 can be configured to model, or otherwise reproduce, the current bite position between the upper and lower teeth 16, 27. For example, in some non-limiting embodiments of the present technology, the processor 550 can be configured to (i) obtain, for example, from the imaging device 430, another 3D digital model of the lower and upper arch form 20, 21 in the current bite position; (ii) register a current mutual position between certain predetermined reference points (not depicted) on the surfaces of the lower and upper arch forms in the current bite position; (iii) obtain the 3D digital model 700 including individual 3D digital models of each one of the upper and lower arch forms 20, 21; (iv) identify, on the surface of the upper and lower arch forms 20, 21 in the 3D digital model 700, the predetermined reference points; and (v) cause movement of at least one of the upper and lower arch forms 20, 21, within the 3D digital model 700, placing the predetermined reference points to the current mutual position.

However, in other non-limiting embodiments of the present technology, the processor 550 can be configured to model the current bite position between the upper and lower arch forms 20, 21 in the 3D digital model 700 using one or more approaches described in a co-owned U.S. Pat. No. 11,364,103-B1, issued on Jun. 21, 2022, entitled "SYSTEMS AND METHODS FOR DETERMINING A BITE POSITION BETWEEN TEETH OF A SUBJECT", the content of which is incorporated herein by reference in its entirety.

More specifically, to determine the current bite position between the upper and lower arch forms 20, 21, the processor 550 can be configured for: (i) determining, for each vertex of a first portion of the 3D model 700, representative of the lower arch form 21, a respective distance value therefrom to a second portion of the 3D model 700, representative of the upper arch form 20; (ii) determining, for each vertex of the first portion of the 3D model 700, a respective weight value, the respective weight value associated with a given vertex of the first portion of the 3D model 700 being indicative of a curvature of a surface of the 3D model thereat; (iii) generating, for each vertex of the first portion of 3D model 700 representative of the lower arch form 21, based on the respective weight value and the respective distance value associated therewith, a respective weighted distance value; aggregating respective weighted distance values associated with each vertex of the first portion thereby determining an aggregate distance value, the aggregate distance value being indicative of a remoteness measure of a current position of the first portion of the 3D model 700 from the current bite position thereof relative to the second portion of the 3D model 700; and minimizing the aggregate distance value to determine the current bite position of the lower arch form 21 and the upper arch form 20.

Further, for determining the tooth trajectories of each one of the upper and lower teeth 16, 27, in some non-limiting embodiments of the present technology, after receiving the 3D digital model 700, the processor 550 may be configured to segment thereon 3D representations of crown portions of the upper and lower teeth 16, 27, such as the crown portion 26 of the given tooth 15.

How the processor 550 can be configured to isolate the crown portion 26 within the 3D digital model 700 is not limited; and, in some non-limiting embodiments of the present technology, the processor 550 can be configured to apply one or more automatic tooth segmentation approaches described in a co-owned U.S. Pat. No. 10,950,061-B1 issued on Mar. 16, 2021, entitled "SYSTEMS AND METHODS FOR PLANNING AN ORTHODONTIC TREATMENT", content of which is incorporated herein by reference in its entirety.

More specifically, in these embodiments, the processor 550 may be configured to: (i) identify, in the 3D digital model 700, an arch form 3D digital model of the upper arch form 20 of the subject, the arch form 3D digital model comprising a defined portion forming part of a surface of the given tooth 15, and at least one undefined portion not forming part of the surface of the given tooth 15; the arch form 3D digital model comprising the plurality of mesh elements having a plurality of vertices comprising: constrained vertices associated with the defined portion, each constrained vertex having a normal constrained vertex vector; unconstrained vertices initially associated with the undefined portion, each unconstrained vertex having a normal unconstrained vertex vector; (ii) generate a set of confirmed constrained vertices, including the constrained vertices associated with the defined portion, for providing a crown 3D digital model of the crown portion 26 of the given tooth 15 by: (iii) iteratively, for a given constrained vertex, identifying at least one associated unconstrained vertex which is adjacent to the given constrained vertex in the plurality of mesh elements; (iv) determining an angular difference between the normal constrained vertex vector of the given constrained vertex and the normal unconstrained vertex vector of the at least one associated unconstrained vertex; (v) in response to the angular difference being equal to or below a predetermined threshold value: identifying the at least one associated unconstrained vertex to be a constrained vertex associated with the defined portion for inclusion in the set of confirmed constrained vertices; (vi) in response to the angular difference being above the predetermined threshold value: identifying the at least one associated unconstrained vertex to be an unconstrained vertex associated with the undefined portion for exclusion from the set of confirmed constrained vertices.

Further, in some non-limiting embodiments of the present technology, the processor 550 can further be configured to generate, based on the representation of the crown portion 26, segmented within the 3D digital model 700 as described above, a root 3D digital model (not depicted in FIG. 7) of the root portion 28 of the given tooth 15. It is not limited how the processor 550 can be configured to reconstruct the root 3D digital model based on the crown 3D digital model of the crown portion 26; and in some non-limiting embodiments of the present technology, the processor 550 can be configured to apply one or more approaches based on reference data associated with the subject, described in a co-owned U.S. Pat. No. 11,026,767-B1 issued on Jun. 8, 2021, and entitled "SYSTEMS AND METHODS FOR PLANNING AN ORTHODONTIC TREATMENT", the content of which is incorporated herein by reference in its entirety.

More specifically, to generate the root 3D digital model of the root portion 28, the processor 550 can be configured for: (i) acquiring the crown 3D digital model of the crown portion 26 of the given tooth 15, generated as described above, the crown 3D digital model being associated with a predetermined longitudinal tooth axis; generating the root 3D digital model of the root portion 28 of the given tooth 15 by executing the steps of: (ii) determining a location of a root apex of the root 3D digital model of the root portion 28 relative to the predetermined longitudinal tooth axis, the determining being based on a predetermined instruction for locating the apex 44 of the root portion 28; (iii) generating, in a reference plane dissecting the predetermined longitudinal tooth axis and based on the crown 3D digital model of the crown portion 26, a closed curve on or around the crown 3D digital model of the crown portion 26, (iv) segmenting the closed curve into a plurality of sub-curves; and (v) for each one of the plurality of sub-curves, based on the apex 44 and the predetermined longitudinal tooth axis, generating a respective segment of a plurality of segments of the root 3D digital model of the root portion 28, the plurality of segments of the root 3D digital model of the root portion 28 comprising a totality thereof.

Figure 8:
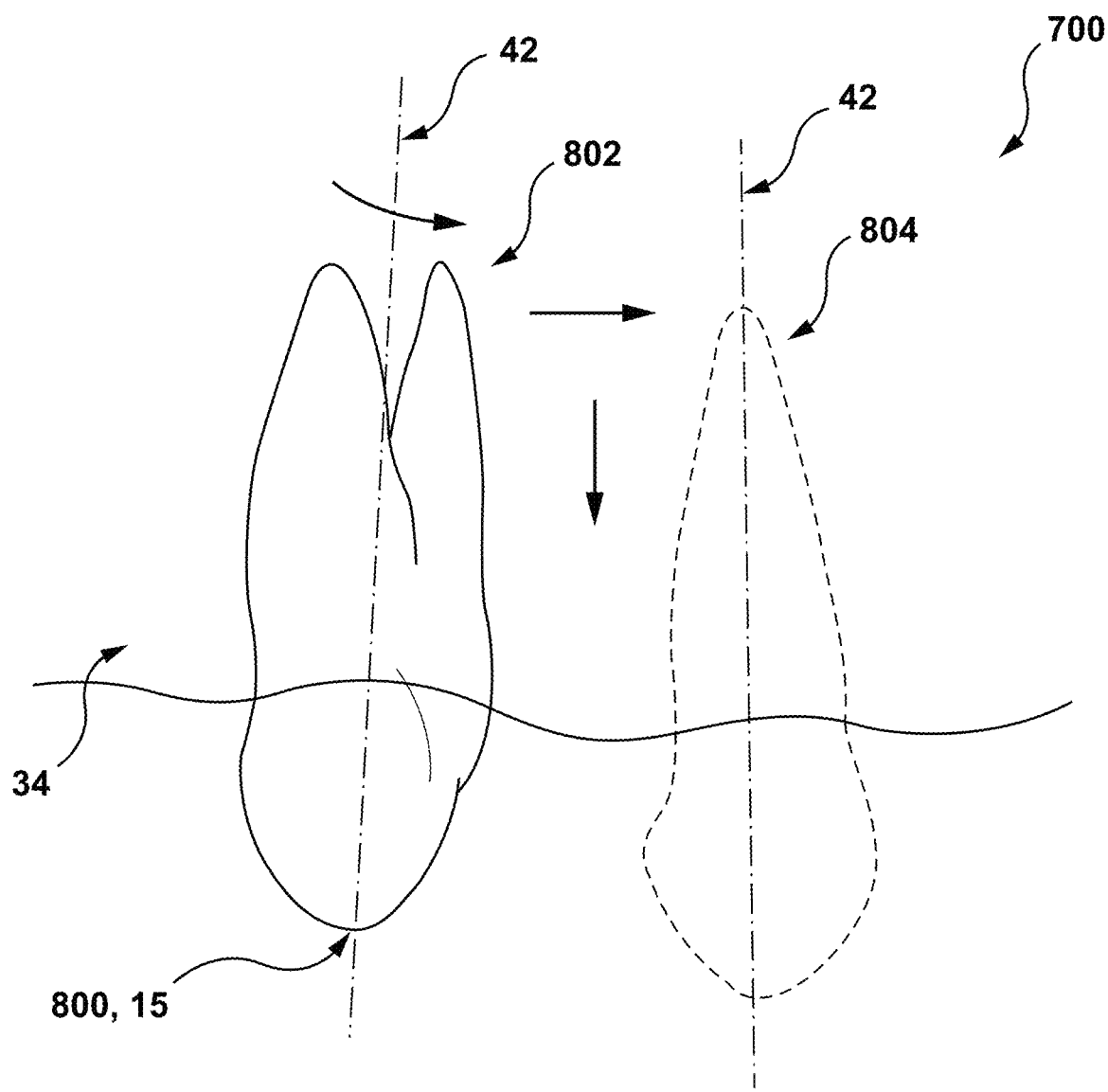
FIG. 8 depicts a schematic diagram of a current and target position of the given tooth of the subject within the 3D digital model of FIG. 7, in accordance with the non-limiting embodiments of the present technology.

Additionally, in some non-limiting embodiments of the present technology, the processor 550 can be configured to merge the crown 3D digital model of the crown portion 26 with the root 3D digital model of the root portion 28, thereby generating a complete 3D digital model of the given tooth 15, such as a tooth 3D digital model 800 depicted in FIG. 8, in accordance with certain non-limiting embodiments of the present technology.

Also, as it will become apparent from the description provided below, according to certain non-limiting embodiments of the present technology, the processor 550 may be configured to determine a coordinate system 750 associated with the 3D digital model 700. In one non-limiting example, the processor 550 may be configured to determine the coordinate system 750 as a Cartesian 3D coordinate system whose an XY plane is parallel to a transverse plane associated with a subject's skull (not depicted). In another example, the XY plane may be parallel to a Frankfort horizontal plane associated with the subject's cranium (not depicted).

Thus, based on the 3D digital model 700, using the coordinate system 750, the processor 550 can be configured to determine a current, or otherwise initial, position of the given tooth 15 in the upper arch form 20, such as a current tooth position 802 and a target tooth position 804 of the given tooth 15 depicted in FIG. 8. It is not limited how the processor 550 can be configured to determine the current position of the given tooth 15. For example, in some non-limiting embodiments of the present technology, the processor 550 can be configured to determine coordinates, in the coordinate system 750, of each vertex of the 3D digital model 700 defining surfaces of at least one of the crown portion 26 and the root portion 28 (not depicted in FIG. 7) of the given tooth 15 in the 3D digital model 700.

However, in other non-limiting embodiments of the present technology, the processor 550 can be configured to determine coordinates of only some vertices of the 3D digital model 700 defining the surfaces of the at least one of crown and root portions 26, 28 of the given tooth 15. For example, such vertices can include center vertices of each one of a labial, lingual, mesial, and distal surfaces (not separately labelled in FIGS. 7 and 8) of the crown portion 26 of the given tooth 15. In another example, such vertices can include vertices representative of a mesial and distal points (not depicted) associated with the crown portion 26 and a vertex representative of the apex 44 of the root portion 28.

In yet other non-limiting embodiments of the present technology, the processor 550 can be configured to determine the current position of the given tooth 15 within the 3D digital model 700 as coordinates, in the coordinate system 750, of a current position of a representative reference object associated with the given tooth 15. In one example, the representative reference object can be coordinates of the CR point 40 associated with the given tooth 15, as depicted in FIGS. 3A to 3D. In another example, the representative reference object can be the tooth axis 42 associated with the given tooth 15, as depicted in FIGS. 3A to 3D.

It is not limited how the processor 550 can be configured to determine the locations of the CR point 40 and the tooth axis 42 of the given tooth 15 in the 3D digital model 700. In some non-limiting embodiments of the present technology, the tooth axis 42 may be predetermined, by the processor 550, based on data indicative of specific anatomical features of crown portion 26 which includes, without limitation: lobes, developmental grooves, and marginal ridges, as an example. In these embodiments, the data indicative of the specific anatomical features of the crown portion 26 may be part of the reference data indicative of the given tooth 15 and include data of spatial positions and dimensions of at least some of the above-listed anatomical features of the crown portion 26 averaged over a certain sample of subjects.

In some non-limiting embodiments of the present technology, the processor 550 can be configured to determine the tooth axis 42 of the given tooth 15 in accordance with one of the approaches described in co-owned U.S. Pat. No. 10,856,954-B1 issued on Dec. 8, 2020, and entitled "SYSTEMS AND METHODS FOR DETERMINING TOOTH CENTER OF RESISTANCE", the content of which is incorporated herein by reference in its entirety.

More specifically, in order to determine the respective the tooth axis 42, the processor 550 can be configured to: (i) receive image data associated with the crown portion 26 of the subject—such as the 3D digital model 700; (ii) identify an internal reference point in the image data, the internal reference point being based on a predetermined internal reference point instruction for locating the internal reference point in the crown portion 26 including obtaining the mesial point on a mesial side of the crown portion 26, and the distal point on a distal side of the crown portion 26; generating a mesiodistal line joining the mesial point and the distal point, and identifying the mesiodistal center as a midpoint on the mesiodistal line; (iii) determine a reference plane in the 3D digital model 700, the reference plane being perpendicular to the mesiodistal line and extending through the mesiodistal center; (iv) determine an intersection curve based on an intersection of the reference plane and a representation of the given tooth 15, the intersection curve following a shape of the surface of the crown of the given tooth 15 at the reference plane; and (v) determine the tooth axis 42 of the crown portion 26 of the given tooth 15 based on the intersection curve.

Further, in some non-limiting embodiments of the present technology, the processor 550 can be configured to (i) determine a height of the root portion 28, either based on the 3D digital model 700, or from reference data associated with the given tooth 15; and (ii) based of the height of the root portion 28, the processor 550 can be configured to determine the location of the CR point 40 on the tooth axis 42, which depending on a type of the given tooth can be at a level from ½ to ⅔ of the height of the root portion 28.

It should further be noted that other representative reference objects associated with the given tooth 15, such as a bounding box or a bounding sphere defined therearound, are also envisioned without departing from the scope of the present technology.

Step 602 ends.

Step 604: Obtaining, by the Processor, an Indication of a Target Position for the Given Tooth At step 604, the processor 550 can be configured to obtain the target position for the given tooth 15, such as the target tooth position 804 as depicted in FIG. 8, to which the given tooth 15 is to be caused to move in the course of the orthodontic treatment. For example, as mentioned above, the target tooth position 804 of the given tooth 15 can be its aligned position within the upper teeth 16. However, in other non-limiting embodiments of the present technology, the target tooth position 804 may be any other desired position of the given tooth 15, such as an intermediate position of the given tooth 15 towards the aligned position or a position thereof allowing for alignment of other teeth of the upper and lower teeth 16, 27, as an example.

In some non-limiting embodiments of the present technology, the target tooth position 804 for the given tooth 15 may be provided by the practicing clinician, such as by manipulating the current position of the given tooth 15 within the 3D digital model 700. In other non-limiting embodiments of the present technology, the processor 550 may be configured to determine the target tooth position 804 based on averaged data associated with aligned teeth received from a group of subjects.

The method 600 hence advances to step 606.

Step 606: Determining, by the Processor, Based on the Current and the Target Position of the Given Tooth, a Tooth Movement Trajectory of the Given Tooth During the Orthodontic Treatment, the Tooth Trajectory Defining a Path of the Given Tooth from the Current to the Target Position Thereof Further, at step 606, based on the current and target tooth positions 804, 806 of the given tooth 15, obtained at the previous steps, the processor 550 can be configured to determine the tooth trajectory for the given tooth 15, defining a path thereof from the current to the target position in the course of the orthodontic treatment.

According to certain non-limiting embodiments of the present technology, the processor 550 can be configured to determine the tooth trajectory based on the required tooth movement of the given tooth 15 from the current and target tooth positions 804, 806. To that end, the processor 550 can be configured to obtain the plurality of tooth movement components defining the tooth movement. As mentioned herein above, a given one of the plurality of tooth movement components is indicative of a respective degree of freedom of the given tooth 15 in the alveolar bone 36. More specifically, the plurality of tooth movement components can include, without limitations at least one of: a translation (as described above with reference to FIG. 3C); a tipping (both controlled and uncontrolled, as described above with reference to FIGS. 3A and 3B, respectively), an axial rotation (such as around the tooth axis 42, not depicted), an extrusion, and an intrusion (both not depicted); a torquing (a labio-lingual movement of the root portion 28 relative to the crown portion 26, not depicted); an uprighting (as described above with reference top FIG. 3D).

It should be expressly understood the above listed plurality of tooth movement components is not an exhaustive list, and other movement components feasible by the given tooth in the current tooth position 802 thereof are also envisioned. Also, it should be expressly understood that the given tooth movement component, such as one of rotational tooth movement components and the tipping, for example, can be executed in both mesiodistal and labiolingual directions.

Depending on the current and target tooth positions 802, 804 of the given tooth 15, according to certain non-limiting embodiments of the present technology, the processor 550 can be configured to determine the tooth movement for the given tooth 15 including at least two tooth movement components of the plurality of tooth movement components mentioned above.

With reference to FIG. 8, there is depicted the tooth 3D digital model 800 representing a distal aspect of the given tooth 15 within the 3D digital model 700 in the current tooth position 802 and the target position 804, in accordance with certain non-limiting embodiments of the present technology.

For example, as it can be appreciated from FIG. 8, to cause the given tooth 15 to move from the current tooth position 802 to the target position 804, the processor 550 can be configured to determine the tooth movement including (i) a counterclockwise axial rotation around the tooth axis 42; (ii) the lingual translation; and (iii) the extrusion of the given tooth 15 from the upper gingiva 34—as indicated in FIG. 8 by bold arrows.

However, it should be expressly understood that, in other non-limiting embodiments of the present technology, the tooth movement of the given tooth 15 can include various combinations of the tooth movement components. Also, in some non-limiting embodiments of the present technology, the tooth movement of the given tooth 15 can include two same tooth movement components, such as two translations, or two tipping movements, for example. In some non-limiting embodiments of the present technology, the tooth movement of the given tooth 15 can include all tooth movement components of the plurality of tooth movement components mentioned above.

Further, it is not limited how the processor 550 can be configured to determine the tooth movement and tooth movement components thereof. In some non-limiting embodiments of the present technology, the processor 550 can be configured to determine the tooth movement components of the tooth movement of the given tooth 15 automatically. To that end, the processor 550 can be configured to apply an alignment algorithm to the tooth 3D digital model 800 of the given tooth 15 in the current and target tooth positions 802, 804 thereof. It is not limited how the alignment algorithm is implemented; and in some non-limiting embodiments of the present technology, the alignment algorithm can include at least one of (i) rigid registration algorithms, including applying rigid transformation to tooth 3D digital model 800, such as translations and rotations; (ii) non-rigid registration algorithms, including applying affine transformations to the tooth 3D digital model 800, such as scaling and shear mapping; (iii) correspondence-based registration algorithms, such as a RANSAC algorithm; (iv) simultaneous pose and correspondence registration algorithms, such as an iterative closest point algorithm (ICP); (v) a Kernel correlation algorithm, and others.

The execution of each one of the above-mentioned types of the alignment algorithm is not the subject of this paper; however, by way of example, in those embodiments where the alignment algorithm is the ICP algorithm, the processor 550 can be configured to execute the following steps: (1) receiving a first tooth 3D digital model, which can be the tooth 3D digital model 800 in the current tooth position 802, and a second tooth 3D digital model, which can be the tooth 3D digital model 800 in the target position 804; (2) for each vertex in the first tooth 3D digital model, selecting a corresponding vertex in the second tooth 3D digital model; (3) minimizing a distance between the selected vertices by applying transformations, such as those corresponding to the plurality of tooth movement components, for example; (4) iteratively repeating steps (2) and (3) until a predetermined condition is reached. In some non-limiting embodiments of the present technology, the predetermined condition may be, for example, a predetermined threshold value of an error metric, which can include a point-to-point error metric or a point-to-plane error metric.

Thus, by applying the alignment algorithm, the processor 550 can be configured to merge the first and second tooth 3D digital models and thus register the applied transformations, corresponding to the respective ones of the plurality of tooth movement components. Further, according to certain non-limiting embodiments of the present technology, the processor 550 can be configured to aggregate the tooth movement components by types thereof, thereby determining respective magnitude values for each of the tooth movement components of the tooth movement of the given tooth 15.

Other automatic approaches to determining the tooth movement components of the given tooth 15, such as those including applying a machine-learning algorithm trained, based on data indicative of tooth movements of past subjects, for example, to determine the tooth movements of the given tooth 15 from the current tooth position 802 to the target tooth position 804, are also envisioned without departing from the scope of the present technology.

However, in other non-limiting embodiments of the present technology, the processor 550 can be configured to obtain indications of each tooth movement components and magnitudes values therefor from the practicing clinician involved in the development of the orthodontic treatment plan. For example, the processor 550 can be configured to register the tooth movement components and magnitudes values thereof as the practicing clinician moves the tooth 3D digital model 800 from the current tooth position 802 to the target position 804. In another example, the practicing clinician can input to the computer system 410, such as using one of the interface device 420 thereof, the magnitude values for each one of the plurality of tooth movement components, thereby defining the tooth movement for the given tooth 15.

In yet other non-limiting embodiments of the present technology, the processor 550 can be configured to determine the tooth movement components for the given tooth 15 automatically, and further obtain corrections thereof from the practicing clinician, such as via respective graphical user interface, as will become apparent from the description provided below.

Thus, based on the so determined tooth movement components defining the tooth movement of the given tooth 15, the processor 550 can be configured to determine the respective forces causing such tooth movement components for further determining the orthodontic treatment plan for the subject.

Figure 9:
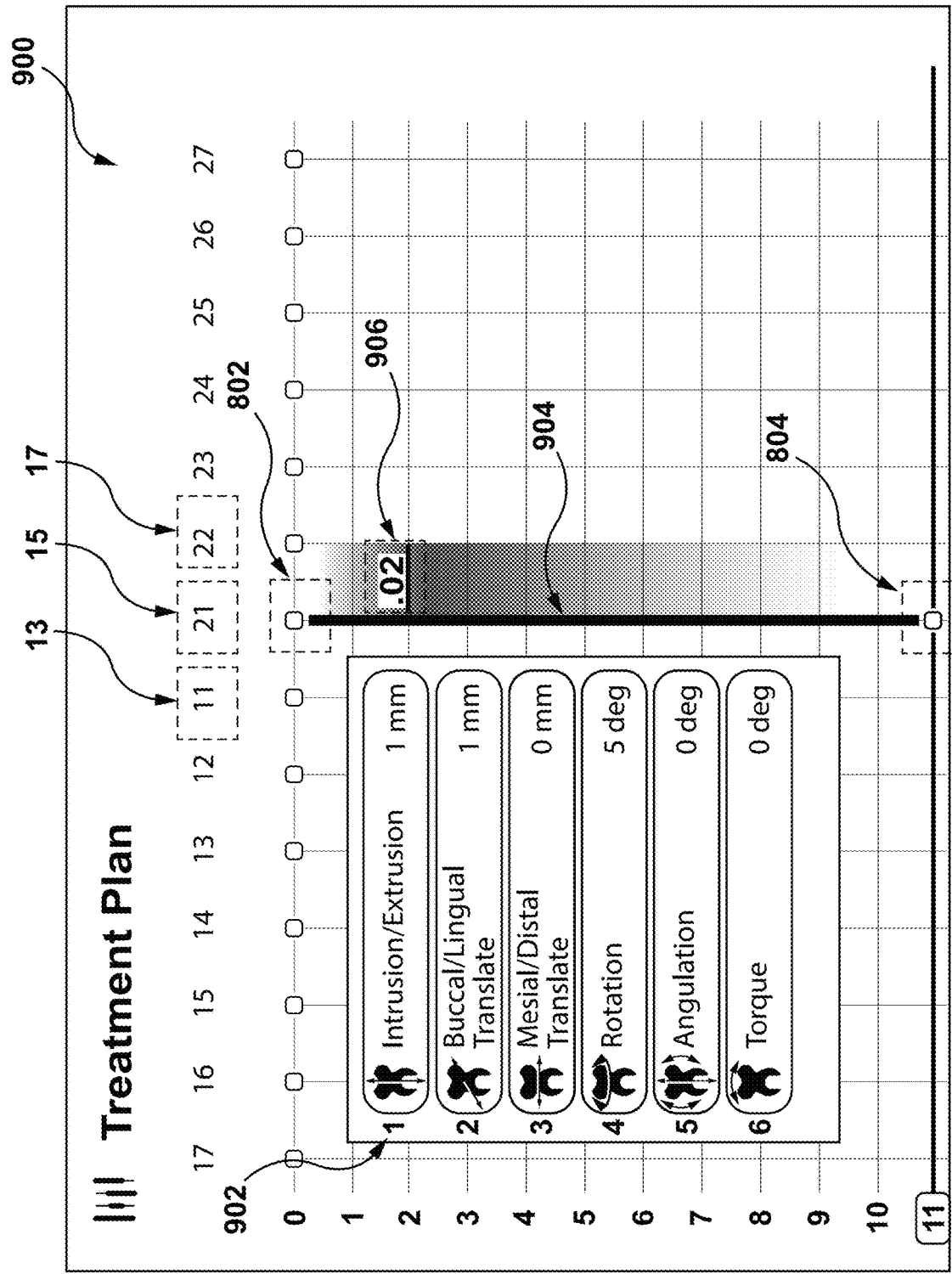
FIG. 9 depicts a schematic diagram of an orthodontic treatment plan for the subject including indications of tooth movements that the given tooth is to perform to move from the current to the target positions depicted in FIG. 8, in accordance with the non-limiting embodiments of the present technology.

With reference to FIG. 9, there is depicted a planning diagram 900 of the orthodontic treatment plan for the subject including movements of the given tooth 15, in accordance with certain non-limiting embodiments of the present technology.

More specifically, the planning diagram 900 includes a horizontal axis representative of respective ordinal numbers of the upper teeth 16 and the lower teeth 27, including the given tooth 15; and a vertical axis representative of a time of the orthodontic treatment. Further, the planning diagram 900 includes a movement schedule 902 associated with the given tooth 15, including the tooth movement components and the respective magnitude values thereof, determined as described above, that define a planned tooth trajectory 904 of the given tooth 15 from the current tooth position 802 to the target tooth position 804.

As it can be appreciated, the respective magnitude value of the given tooth movement component is thus indicative of a path length, at which the given tooth 15 is to be caused to displace, when performing the given tooth movement component. More specifically, according to the planning diagram 900, during the orthodontic treatment, to reach the target tooth position 804, the given tooth 15 is to perform: (i) the extrusion from the upper gingiva 34 at 1 mm; (ii) the lingual translation at 1 mm; and (iii) the counterclockwise axial rotation at 5 degrees.

Also, in some non-limiting embodiments of the present technology, the planning diagram 900 can further display a collision value 906 indicative of a depth of a collision (if any has occurred) between the given tooth 15 and, for example, one of the first and second adjacent teeth 13, 17. In the embodiments depicted in FIG. 9, the collision value 906 is 0.2 mm and is displayed in a beginning of the planned tooth trajectory 904, which is to mean that the collision having depth of 0.2 mm with the one of the first and second adjacent teeth 13, 17 is possible in the beginning of the planned tooth trajectory 904 given a current version of the orthodontic treatment plan.

Further, according to certain non-limiting embodiments of the present technology, the processor 550 can be configured to determine, for each one of the tooth movement components associated with the given tooth 15, a respective ordinal position thereof in the movement schedule. For example, in some non-limiting embodiments of the present technology, the processor 550 can be configured to determine the ordinal position for each one of the tooth movement components automatically. In some non-limiting embodiments of the present technology, the processor 550 can be configured to determine the respective ordinal position based on a predetermined priority values of each one of the plurality of tooth movement components that the given tooth 15 can have. For example, translational tooth movement components, such as the translation, the extrusion, or the intrusion can have a higher priority over rotational tooth movement components, such as the tipping or the axial rotation, as an example. Assigning different predetermined priorities to each one of the plurality of tooth movement components individually is also envisioned without departing from the scope of the present technology.

Also, in other non-limiting embodiments of the present technology, the processor 550 can be configured to determine the respective ordinal position for each one of the tooth movement components in the movement schedule 902 such that a predetermined condition is met. In some non-limiting embodiments of the present technology, the predetermined condition can be minimization of the collision value 906 along the planned tooth trajectory 904, as an example.

In other non-limiting embodiments of the present technology, the processor 550 can be configured to obtain the respective ordinal position for each one of the tooth movement components in the movement schedule 902 from the practicing clinician who determines the respective ordinal position, for example, based on their experience and expertise in developing orthodontic treatments.

Also, in some non-limiting embodiments of the present technology, as it can be appreciated, the processor 550 can be configured to cause display of the planning diagram 900, for example, in the screen 422 of the computer system 410, as part of a graphical user interface (GUI) of a treatment planning application, for example, for aiding the practicing clinician in determining and/or monitoring the current version of the orthodontic treatment plan, including the planned tooth trajectory 904.

Further, according to certain non-limiting embodiments of the present technology, the processor 550 can be configured to model the tooth movement components having been determined in the movement schedule 902 in order to determine the respective forces to impose on the given tooth 15 during the orthodontic treatment. These forces, when applied to the given tooth 15, for example, via a respective configuration of the aligner 10, would cause the given tooth 15 to perform respective tooth movement components.

It is not limited how the processor 550 can be configured to model each one of the tooth movement components of the given tooth 15; and in some non-limiting embodiments of the present technology, the processor 550 can be configured to apply one or more approaches of determining the respective forces based on admissible stress values applied to the periodontal ligament 38 of the given tooth 15, as described in a co-owned U.S. Pat. No. 10,993,782-B1 issued on May 4, 2021, and entitled "SYSTEMS AND METHODS FOR DETERMINING A TOOTH TRAJECTORY", a content of which is hereby incorporated by reference in its entirety.

However, it should be noted that use of other approaches to determining the respective forces is also envisioned, which can include, for example, determining the respective forces in response to the desired tooth movements based on a finite element model (FEM) simulating mechanical properties of the given tooth 15 and the tissues of the periodontium 30 thereof, as described, for example, in an article "A Biomechanical Case Study on the Optimal Orthodontic Force on the Maxillary Canine Tooth Based on Finite Element Analysis" authored by Jian-lei Wu, Yun-feng Liu, Wei Peng, Hui-yue Dong, and Jian-xing Zhang, and published in Journal of Zhejiang University-SCIENCE B (Biomedicine & Biotechnology).

Further, according to certain non-limiting embodiments of the present technology, the processor 550 can be configured to model each one of the tooth movement components separately, without any combination thereof with other tooth movement components. In other words, the processor 550 can be configured to model the tooth movement components of the given tooth 15 such that the so determined respective forces would cause the given tooth 15 to perform only a single tooth movement component in the given moment in time. For example, the processor 550 can be configured to model each one of the tooth movement components in the movement schedule 902 sequentially, in accordance with the previously determined respective ordinal positions thereof.

Figure 10:
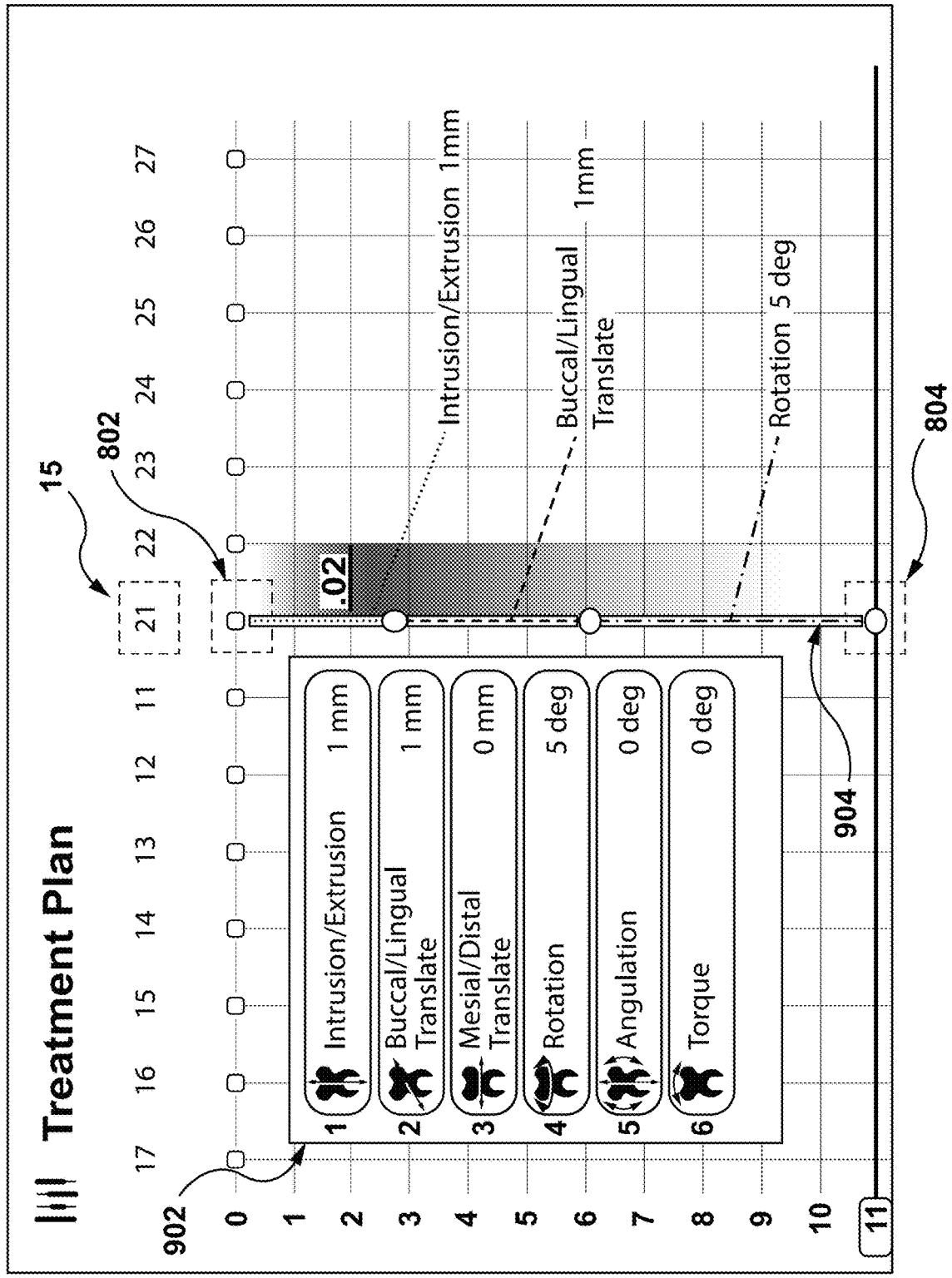
FIG. 10 depicts a schematic diagram of the orthodontic treatment plan including indications of modelling, by the processor of FIG. 5, the tooth movements to determine a tooth trajectory of the given tooth, in accordance with the non-limiting embodiments of the present technology.

With reference to FIG. 10, there is depicted the planning diagram 900 with an indication of a separate modelling, by the processor 550, of each one of the tooth movement components of the given tooth 15, in accordance with certain non-limiting embodiments of the present technology.

More specifically, in the embodiments depicted in FIG. 10, the processor 550 can be configured to separately model: (i) the extrusion of the given tooth 15 at 1 mm to determine a first force; (ii) the buccal translation at 1 mm to determine a second force; and (iii) the counterclockwise axial rotation of the given tooth 15 at 5 degrees to determine a third force. As mentioned above, the processor 550 can be configured to model each of these tooth movement components sequentially, in any order. Thus, the processor 550 can be configured to determine the respective forces, an individual application of which can cause the given tooth 15 to perform a separate one of the tooth movement components determined in the movement schedule 902.

Also, in some non-limiting embodiments of the present technology, when determining the respective forces to apply to the given tooth 15, the processor 550 can be configured to factor in a desired respective speed value for each one of the tooth movement components of the given tooth 15 determined in the movement schedule 902.

In some non-limiting embodiments of the present technology, the processor 550 can be configured to determine the respective speed value for the given tooth movement component of the tooth movement components based on a predetermined threshold displacement of the given tooth 15, when performing the given tooth movement component, in a given time interval. The given time interval may have a duration of 1 day, 10 days, or 20 days, as an example. In some non-limiting embodiments of the present technology, the given time interval can be predetermined, and comprise, for example, 14 days. By doing so, the processor 550 can be configured to define, along the vertical axis of the planning diagram 900 a plurality of time intervals (not separately labelled). As it can be appreciated, in these embodiments, each one of the plurality of time intervals has an equal duration.

Further, in some non-limiting embodiments of the present technology, the predetermined threshold displacement of the given tooth 15 can be determined as a maximum predetermined displacement of the given tooth 15 that would not cause permanent damage thereto or to the tissues of the periodontium 30 thereof, such as the periodontal ligament 38, as an example. However, it should be noted that other considerations in selecting the predetermined threshold displacement of the given tooth 15 are also envisioned and can include, for example, individual sensitivity of the subject to the orthodontic treatment, current medical problems (such as gingivitis or osteoporosis, as an example), and the like, in which case the predetermined threshold displacement can be adjusted such that the orthodontic treatment would not cause pain to the subject and/or exacerbate their current health problems.

Thus, by modelling the tooth movement components of the given tooth 15 considering the predetermined threshold displacement thereof in the given time interval, the processor 550 can be configured to divide each one of the tooth movement components in a respective number of portions, each of which would define a respective segment of a plurality of segments of the planned tooth trajectory 904. Further, a given segment of the plurality of segments of the planned tooth trajectory 904 corresponds to a respective one of the plurality of time intervals. Thus, instead of performing the given tooth movement component at once, the given tooth 15 may be caused to perform the respective number of portions thereof, along at least one segment (or some thereof) of the plurality of segments of the planned tooth trajectory 904.

More specifically, in the example of FIG. 10, the planned tooth trajectory 904 of the given tooth includes: (i) three segments for the extrusion of the given tooth 15; (ii) three segments for the lingual translation of the given tooth 15; and (iii) five segments for the counterclockwise axial rotation of the given tooth 15 around the tooth axis 42.

Accordingly, in some non-limiting embodiments of the present technology, based on the so defined portions of each one of the tooth movement components that the given tooth 15 is to be caused to perform in the respective one of the plurality of time intervals, the processor 550 can be configured to determine the respective forces, as mentioned above, causing the given tooth 15 to move along the respective segments of the plurality of segments of the planned tooth trajectory 904. Such a force can thus cause the given tooth 15 to displace, in the given time interval, at the predetermined threshold displacement, performing the respective portion of the given tooth movement component, which defines the respective segment of the plurality of segments of the planned tooth trajectory 904.

The method 600 hence advances to step 608.

Step 608: Storing, in a Memory of the Computing Device, Data of the Tooth Trajectory of the Given Tooth for Further Use in Determining the Orthodontic Treatment for the Subject Further, at step 608, the processor 550 can be configured to store data of the planned tooth trajectory 904 and the respective forces to be applied along each one of the plurality of segments thereof in a memory of the computer system 410, such as the solid-state drive 560.

Further, in some non-limiting embodiments of the present technology, based on this data, the processor 550 can be configured to cause the manufacturing system 440 to manufacture the at least one configuration of the aligner 10, as described above, whose inner surface 12 is configured to cause the given tooth 15 to perform the respective tooth movement component of the tooth movement components defined in the movement schedule 902. For example, in some non-limiting embodiments of the present technology, during a given stage of the orthodontic treatment, for causing the given tooth 15 to move along the respective segment of the planned tooth trajectory 904, a distinct configuration of the aligner 10 can be applied.

More specifically, in some non-limiting embodiments of the present technology, a given configuration of the aligner 10 thus produced can be configured to exert the respective force, determined as described above, on the given tooth 15 causing it to perform, in the given time interval, the respective portion of the given tooth movement component, along the respective segment of the plurality of segments of the planned tooth trajectory 904.

The method 600 thus terminates.

Thus, certain non-limiting embodiments of the method 600 allow modelling and further causing, by the respective configurations of the aligner 10, the movements of the given tooth 15 as the plurality of tooth movement components that are to be performed separately. This may simplify the planning process of the orthodontic treatment and hence increase the accuracy thereof, minimizing the deviation between the planned tooth trajectory 904 and the actual tooth trajectory, along which the given tooth 15 would be moving during the course of the orthodontic treatment.

Accordingly, due to the elevated reliability of the orthodontic treatment plan, a greater efficacy of the treatment can be attained.

It should be expressly understood that not all technical effects mentioned herein need to be enjoyed in each and every embodiment of the present technology.

Modifications and improvements to the above-described implementations of the present technology may become apparent to those skilled in the art. The foregoing description is intended to be exemplary rather than limiting. The scope of the present technology is therefore intended to be limited solely by the scope of the appended claims.

The invention claimed is:

1. A computer-implementable method of manufacturing orthodontic appliances for an orthodontic treatment for a subject, the method being executable by a processor of a computing device, the method comprising:
    obtaining, by the processor, a 3D digital model representing a surface of an arch form of the subject, the arch form including a plurality of teeth;
    determining, by the processor, based on the 3D digital model, a current position of a given tooth of the plurality of teeth within the arch form;
    obtaining, by the processor, an indication of a target position for the given tooth;
    determining, by the processor, based on the current and the target position of the given tooth, a tooth movement trajectory of the given tooth during the orthodontic treatment, the tooth trajectory defining a path of the given tooth from the current to the target position thereof, the determining the tooth trajectory comprising determining a movement of the given tooth along the tooth trajectory by:
        determining, by the processor, a plurality of movement components for the given tooth to be performed to displace from the current to the target position;
        obtaining, for a given one of the plurality of movement components, a respective magnitude value,
            the respective magnitude value being indicative of a path length at which the given tooth is to displace towards the target position thereof performing the given one of the plurality of movement components; and
    based on the determined tooth trajectory, causing, by the processor, manufacturing of at least one orthodontic appliance using a manufacturing system, for implementing a respective stage of the orthodontic treatment, the at least one orthodontic appliance being configured to cause the given tooth of the subject to perform at least one portion of the given one of the plurality of movement components during the respective stage of the orthodontic treatment.

2. The method of claim 1, wherein the given one of the plurality of movement components is indicative of a respective degree of freedom of the given tooth within the arch form.

3. The method of claim 2, wherein the given one of the plurality of movement components comprises one of a translation and a rotation.

4. The method of claim 2, wherein the given one of the plurality of movement components comprises one of: a translation; a tipping, a torquing, a rotation, an extrusion, and an intrusion.

5. The method of claim 1, wherein the obtaining, for the given one of the plurality of movement components, the respective magnitude value comprises obtaining the respective magnitude value for at least two ones of the plurality of movement components.

6. The method of claim 5, wherein the obtaining, for the given one of the plurality of movement components, the respective magnitude value comprises obtaining the respective magnitude value for each one of the plurality of movement components.

7. The method of claim 6, wherein the plurality of movement components includes at least two of: a translation; a tipping, a torquing, a rotation, an extrusion, and an intrusion.

8. The method of claim 6, wherein the plurality of movement components comprises the translation and the rotation.

9. The method of claim 5, wherein the orthodontic treatment comprises causing the given tooth to perform each one of the plurality of movement components separately, without combining any one thereof.

10. The method of claim 5, wherein the orthodontic treatment comprises causing the given tooth to perform each one of the plurality of movement components sequentially.

11. The method of claim 1, wherein the obtaining, for the given one of the plurality of movement components, the respective magnitude value comprises determining, by the processor, the respective magnitude value based on minimizing a time for the given tooth to displace from the current to the target position.

12. The method of claim 1, wherein, prior to the storing, the method further comprises obtaining, for the given one of the plurality of movement components, a respective ordinal position thereof within the plurality of movement components of the tooth trajectory.

13. The method of claim 1, wherein, prior to the storing, the method further comprises obtaining, for the given one of the plurality of movement components, a respective speed value at which the given tooth is to be caused to perform the given one of the plurality of movement components.

14. The method of claim 13, wherein the respective speed value is determined based on a predetermined threshold displacement of the given tooth in a given time interval of a plurality of time intervals of the orthodontic treatment, the plurality of treatment intervals defining, within the tooth trajectory for the given tooth, a plurality of segments of the tooth trajectory,
a given segment of the plurality of segments having a respective portion of the path length at which the given tooth is to displace performing the given one of the plurality of movement components in the given time interval.

15. The method of claim 14, wherein the predetermined threshold displacement has been determined as being a maximum displacement of the given tooth in the given time interval without causing a permanent damage to the given tooth.

16. The method of claim 14, wherein the respective portion of the path length is equal to the predetermined threshold displacement.

17. The method of claim 14, wherein the given time interval has a predetermined duration.

18. The method of claim 14, wherein the orthodontic treatment comprises applying, to at least some of the plurality of teeth, during the given time interval, a respective orthodontic appliance configured to cause the given tooth to displace at the respective portion of the path length by performing the given one of the plurality of movement components.

19. The method of claim 18, wherein the respective orthodontic appliance comprises an orthodontic aligner.

20. A computing device for manufacturing orthodontic appliances for an orthodontic treatment for a subject, the computing device comprising a processor and a non-transitory computer-readable memory storing instructions, the processor, upon executing the instructions, being configured to:
obtain a 3D digital model representing a surface of an arch form of the subject, the arch form including a plurality of teeth;
determine, based on the 3D digital model, a current position of a given tooth of the plurality of teeth within the arch form;
obtain an indication of a target position for the given tooth;
determine, based on the current and the target position of the given tooth, a tooth movement trajectory of the given tooth during the orthodontic treatment, the tooth trajectory defining a path of the given tooth from the current to the target position thereof, determining the tooth trajectory comprising determining a movement of the given tooth along the tooth trajectory by:
determining, a plurality of movement components for the given tooth to be performed to displace from the current to the target position;
obtaining, for a given one of the plurality of movement components, a respective magnitude value,
the respective magnitude value being indicative of a path length at which the given tooth is to displace towards the target position thereof performing the given one of the plurality of movement components; and
based on the determined tooth trajectory, cause manufacturing of at least one orthodontic appliance using a manufacturing system, for implementing a respective stage of the orthodontic treatment, the at least one orthodontic appliance being configured to cause the given tooth of the subject to perform at least one portion of the given one of the plurality of movement components during the respective stage of the orthodontic treatment.

* * * * *